US011079331B2

(12) United States Patent
Matsuo et al.

(10) Patent No.: US 11,079,331 B2
(45) Date of Patent: Aug. 3, 2021

(54) INSPECTION SYSTEM

(71) Applicant: Konica Minolta, Inc., Tokyo (JP)

(72) Inventors: Masataka Matsuo, Hachioji (JP); Tetsuya Noda, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 279 days.

(21) Appl. No.: 15/772,346

(22) PCT Filed: Nov. 2, 2016

(86) PCT No.: PCT/JP2016/082643
§ 371 (c)(1),
(2) Date: Apr. 30, 2018

(87) PCT Pub. No.: WO2017/082142
PCT Pub. Date: May 18, 2017

(65) Prior Publication Data
US 2018/0321151 A1  Nov. 8, 2018

(30) Foreign Application Priority Data
Nov. 13, 2015 (JP) .............................. JP2015-223369

(51) Int. Cl.
*G01N 21/64* (2006.01)
*G01N 21/01* (2006.01)
(Continued)

(52) U.S. Cl.
CPC ........... *G01N 21/648* (2013.01); *G01N 21/01* (2013.01); *G01N 21/0332* (2013.01);
(Continued)

(58) Field of Classification Search
CPC ...... G01N 21/648; G01N 35/00; G01N 35/10; G01N 21/0332; G01N 21/11; G01N 21/05;
(Continued)

(56) References Cited

U.S. PATENT DOCUMENTS

2002/0055111 A1  5/2002 Chen et al.
2006/0127951 A1* 6/2006 Ogura .............. G01N 33/54373
435/7.1
(Continued)

FOREIGN PATENT DOCUMENTS

JP  S56172762 U  12/1981
JP  S62168056 A   7/1987
(Continued)

OTHER PUBLICATIONS

EPO, Office Action for the corresponding European patent application No. 16864105.8, dated Mar. 26, 2020.
(Continued)

*Primary Examiner* — Kathryn Wright
*Assistant Examiner* — Curtis A Thompson
(74) *Attorney, Agent, or Firm* — Lucas & Mercanti, LLP

(57) ABSTRACT

To provide an inspection system capable of performing a target biological reaction under temperature conditions suitable for the reaction even with reciprocal liquid feeding. An inspection system including at least: a sensor chip with a flow path having a reaction site for performing biological reactions; a liquid feeder that causes reaction liquid to flow into and out of the flow path; and a first temperature adjuster that adjusts temperature of reaction liquid flowed in the flow path, where the system performs reciprocal liquid feeding by the liquid feeder where some of the reaction liquid flowed in the flow path is caused to flow out of the flow path and to flow in again. The inspection system includes a second
(Continued)

temperature adjuster that, during reciprocal liquid feeding, adjusts temperature of the reaction liquid flowed outside the flow path through temperature adjustment of a liquid holding section of the liquid feeder.

14 Claims, 14 Drawing Sheets

(51) Int. Cl.
| | |
|---|---|
| *G01N 35/00* | (2006.01) |
| *G01N 35/10* | (2006.01) |
| *G01N 21/03* | (2006.01) |
| *G01N 21/11* | (2006.01) |
| *G01N 21/05* | (2006.01) |
| *G01N 35/02* | (2006.01) |
| *G01N 35/04* | (2006.01) |
| *G01N 21/49* | (2006.01) |
| *G01N 33/53* | (2006.01) |
| *G01N 37/00* | (2006.01) |
| *C40B 30/04* | (2006.01) |
| *C40B 40/10* | (2006.01) |
| *G01N 21/77* | (2006.01) |
| *G01N 21/61* | (2006.01) |

(52) U.S. Cl.
CPC ............ *G01N 21/05* (2013.01); *G01N 21/11* (2013.01); *G01N 35/00* (2013.01); *G01N 35/10* (2013.01); *C40B 30/04* (2013.01); *C40B 40/10* (2013.01); *G01N 21/49* (2013.01); *G01N 21/61* (2013.01); *G01N 21/77* (2013.01); *G01N 33/53* (2013.01); *G01N 35/02* (2013.01); *G01N 35/04* (2013.01); *G01N 37/00* (2013.01); *G01N 2021/6482* (2013.01)

(58) Field of Classification Search
CPC ........ G01N 21/01; G01N 21/61; G01N 21/77; G01N 33/53; G01N 37/00; G01N 35/02; G01N 35/04; G01N 21/49; G01N 2021/6482; C40B 30/04; C40B 40/10
See application file for complete search history.

(56) References Cited

U.S. PATENT DOCUMENTS

| | | | | |
|---|---|---|---|---|
| 2013/0312546 | A1* | 11/2013 | Wada | G01N 33/48707 |
| | | | | 73/864.11 |
| 2014/0030151 | A1* | 1/2014 | Horii | G06F 1/206 |
| | | | | 422/69 |
| 2014/0118747 | A1* | 5/2014 | Aoki | G01N 21/553 |
| | | | | 356/445 |
| 2014/0193893 | A1* | 7/2014 | Ishizawa | G01N 35/04 |
| | | | | 435/287.2 |
| 2014/0295450 | A1* | 10/2014 | Morita | G01N 35/00 |
| | | | | 435/6.14 |
| 2015/0316532 | A1* | 11/2015 | Making | G01N 35/1002 |
| | | | | 422/64 |

FOREIGN PATENT DOCUMENTS

| | | |
|---|---|---|
| JP | 2004-061173 A | 2/2004 |
| JP | 2006-105913 A | 4/2006 |
| JP | 2011-099681 A | 5/2011 |
| JP | 2015-148500 A | 8/2015 |
| WO | 2014/103744 A1 | 7/2014 |
| WO | 2015/064757 A1 | 5/2015 |

OTHER PUBLICATIONS

JPO, Office Action for the corresponding Japanese patent application No. 2017-550283, dated Jan. 7, 2020, with English translation.
International Search Report dated Jan. 24, 2018 from corresponding International Application No. PCT/JP2016/082643 and English translation.
Written Opinion of the International Searching Authority dated Jan. 24, 2018 from corresponding International Application No. PCT/JP2016/082643 and English translation.
Extended European Search Report dated Jul. 23, 2018 from corresponding European Application No. 16864105.8.
JPO, Office Action for the corresponding Japanese patent application No. 2017-550283, dated May 19, 2020, with English translation.

* cited by examiner (A)

(B)

INSPECTION SYSTEM

CROSS REFERENCE TO RELATED APPLICATION

This Application is a 371 of PCT/JP2016/082643 filed on Nov. 2, 2016 which, in turn, claimed the priority of Japanese Patent Application No. JP 2015-223369 filed on Nov. 13, 2015, both applications are incorporated herein by reference.

TECHNOLOGICAL FIELD

The present invention relates to an inspection system, for example, an inspection system that utilizes surface plasmon resonance to detect the presence of specimens relating to a disease included in a specimen liquid obtained by biopsy.

BACKGROUND

Inspection systems that utilize surface plasmon resonance are conventionally known for acquiring data for diagnosis of a variety of diseases (for example, in PTL 1).

The inspection system disclosed in PTL 1 includes a detection chip (a sensor chip) for conducting a biological reaction necessary for diagnosis of a disease and a detection device (SPFS device) for detecting, after the sensor chip is set, the above biological reaction by surface plasmon field-enhanced fluorescence spectroscopy (SPFS).

This sensor chip has a minute-flow-path with an inlet and an outlet open for immunoassay. The bottom of this flow path includes a dielectric member, a metallic thin film formed over the upper surface of the dielectric member, and a minute-flow-path constituting member provided on the metallic thin film.

Antibodies (ligands) or the like are immobilized on at least part of the metallic thin film, where, for example, if a blood sample (a specimen liquid) taken from a patient, is injected into the reaction site, biomolecules (relevant to a specific disease) included in the specimen liquid are specifically captured by the immobilized antibodies by means of antigen-antibody reaction. Subsequently, fluorescent-labeled secondary antibodies are specifically bonded with other parts (epitopes) than the antibody-bonded parts of the captured biomolecules, then, the inspection device detects whether the captures have occurred by surface plasmon field-enhanced fluorescence spectroscopy (SPFS), thereby detecting whether the biomolecules are included in the biopsy sample. It should be noted that a predetermined area where ligands are immobilized for a biological reaction is referred to as the "reaction site."

CITATION LIST

Patent Literature

PTL 1: Japanese Unexamined Patent Application Publication No. 2015-148500

SUMMARY

Technical Problem

The above-described biological reaction occurs at the reaction site of the sensor chip, and the temperature of the reaction site is regulated to a temperature suitable for the biological reaction by a heater or the like since the efficiency of the biological reaction is fluctuated depending on the temperature of the reaction liquid at the reaction site (temperature of the reaction site).

By examining the conventional inspection systems, the inventors have found that, when reciprocal liquid feeding, where at least some of a reaction liquid that has flowed in the flow path of the sensor chip is caused to flow out of the flow path and to flow in again, is performed to increase the efficiency of a biological reaction, there are the following problems: (1) in the reciprocal liquid feeding, when the reaction liquid flows out of the flow path and is exposed to a temperature environment different from the temperature in the flow path (e.g., a temperature environment that is lower than the temperature in the flow path due to the influence of the temperature in the SPFS device), the temperature of the reaction liquid changes, and, when this reaction liquid flows in the flow path again, the temperature of the reaction site inside the flow path changes, deviating from a target temperature suitable for the biological reaction; and (2) in one reciprocal liquid feeding, since the temperature of the reaction site is fluctuated each time the reciprocal liquid feeding is performed, the target biological reaction is not performed under appropriate temperature conditions. Accordingly, the inventors have completed the present invention.

In other words, the present invention has been contemplated in consideration of the above problems and aims to provide an inspection system where a target biological reaction can be acquired under temperature conditions suitable for the biological reaction even if reciprocal liquid feeding is performed.

Solution to Problem

To realize at least one of the above objectives, the inspection system of the present invention includes:

a sensor chip equipped with a flow path having a reaction site for a biological reaction in at least part of the flow path;

a liquid feeder that causes a reaction liquid used for the biological reaction to flow in and flow out of the flow path of the sensor chip; and a first temperature adjuster that adjusts a temperature of the reaction liquid that has flowed in the flow path, in which the inspection system performs, by the liquid feeder, liquid feeding where at least some of the reaction liquid that has flowed in the flow path is caused to flow out of the flow path and to flow in again, thereby moving reciprocally (reciprocal liquid feeding), and the inspection system further including: a second temperature adjuster that, during the reciprocal liquid feeding, adjusts a temperature of the reaction liquid that has flowed out of the flow path of the sensor chip through temperature adjustment of a section of the liquid feeder for holding liquid (a liquid holding section).

Advantageous Effects of Invention

According to the present invention, an inspection system is provided, capable of performing a target biological reaction under temperature conditions suitable for the biological reaction even if reciprocal liquid feeding is performed.

DETAILED DESCRIPTION OF EMBODIMENTS

Figure 1:
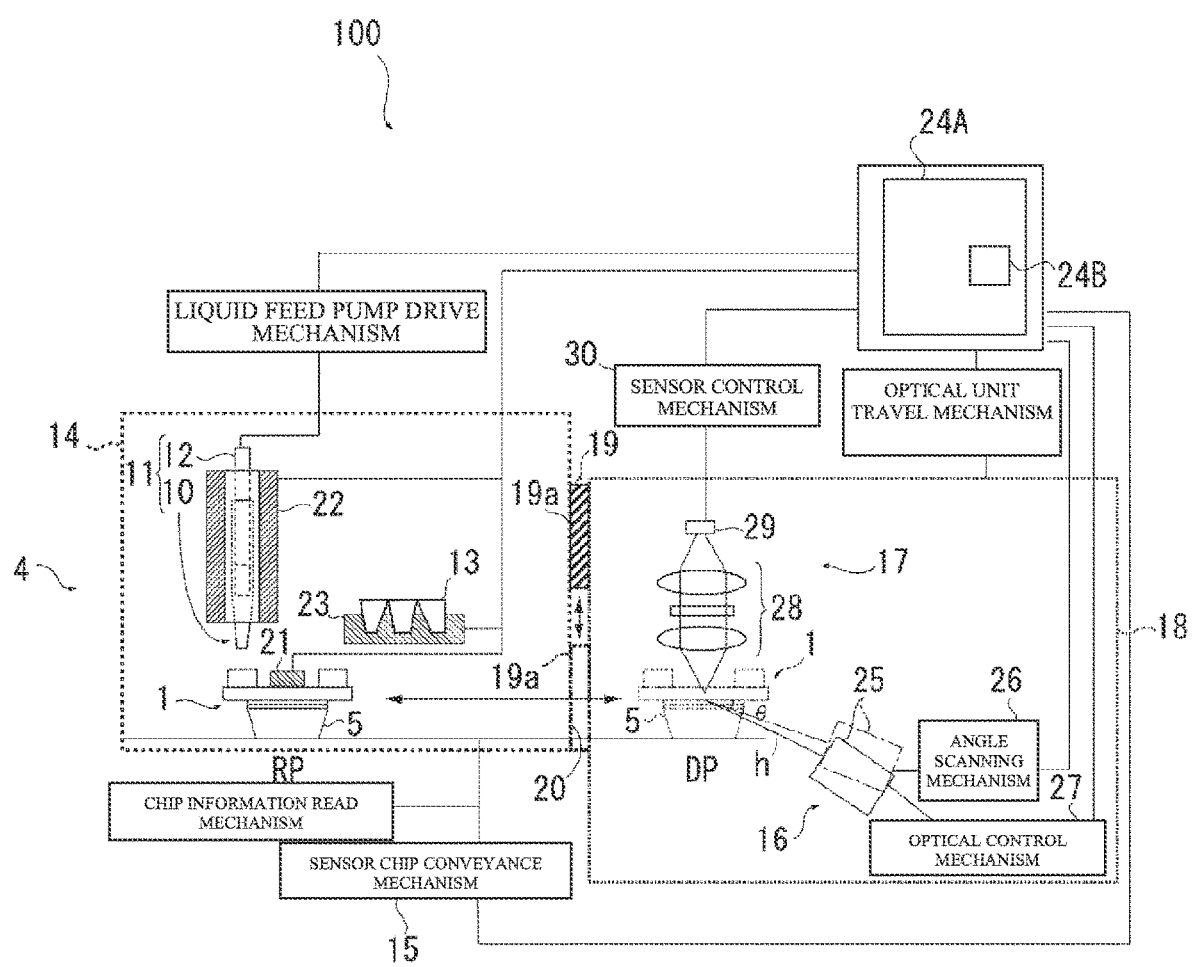
FIG. 1 is a view schematically showing the whole picture of the inspection system according to a first embodiment of the present invention.

The inspection system of the present invention includes the following:

[1] An inspection system at least including:

a sensor chip equipped with a flow path having a reaction site for a biological reaction in at least part of the flow path;

a liquid feeder that causes a reaction liquid used for the biological reaction to flow in and flow out of the flow path of the sensor chip; and a first temperature adjuster that adjusts a temperature of the reaction liquid that has flowed in the flow path, in which the inspection system performs, by the liquid feeder, liquid feeding where at least some of the reaction liquid that has flowed in the flow path is caused to flow out of the flow path and to flow in again, thereby moving reciprocally (reciprocal liquid feeding), and the inspection system further including: a second temperature adjuster that, during the reciprocal liquid feeding, adjusts a temperature of the reaction liquid that has flowed out of the flow path of the sensor chip through temperature adjustment of a section of the liquid feeder for holding liquid (a liquid holding section).

[2] The inspection system according to [1], in which the liquid feeder includes:

a pump for feeding or sucking the reaction liquid to and from the flow path of the sensor chip; and a pipette tip as the liquid holding section attached to the pump, wherein the entire periphery of the pipette tip is covered with a heat block as the second temperature adjuster.

[3] The inspection system according to [2], in which the heat block has an opening.

[4] The inspection system according to [2], in which the sensor chip has a liquid discharger/suction unit that is provided with a space that communicates with the flow path and can house the tip end of the pipette tip, and only part of the pipette tip is covered with the heat block so that at least the tip end of the pipette tip, which is inserted in the space of the liquid discharger/suction unit, is exposed.

[5] The inspection system according to any one of [1] to [4], including:

a liquid reservoir that reserves the reaction liquid; and a third temperature adjuster that adjusts a temperature of the reaction liquid that is reserved in the liquid reservoir before liquid-feeding, in which the third temperature adjuster adjusts the temperature of the reaction liquid before the liquid-feeding to the same temperature as adjusted by the first temperature adjuster.

[6] The inspection system according to any one of [1] to [5], including:

a liquid feed reaction chamber for, when the liquid feeder and sensor chip are arranged inside the liquid feed reaction chamber, at least performing the biological reaction and temperature adjustments by the first to third temperature adjusters, an optical measurement chamber for, when the sensor chip after the biological reaction, a light-emitting unit that irradiates the reaction site of the sensor chip with excitement light, and a light-receiving unit that detects light emitted from the irradiated sensor chip are arranged inside the optical measurement chamber, performing optical measurement based on the detected light, and a partition that opens and closes an opening that makes the liquid feed reaction chamber and the optical measurement chamber to communicate with each other, wherein the partition closes the opening during the biological reaction or the optical measurement.

[7] The inspection system according to [6], in which a temperature of a space inside the optical measurement chamber is set lower than a temperature of a space inside the liquid feed reaction chamber during a biological reaction.

First Embodiment

An inspection system according to a first embodiment of the present invention will be described.

Figure 2:
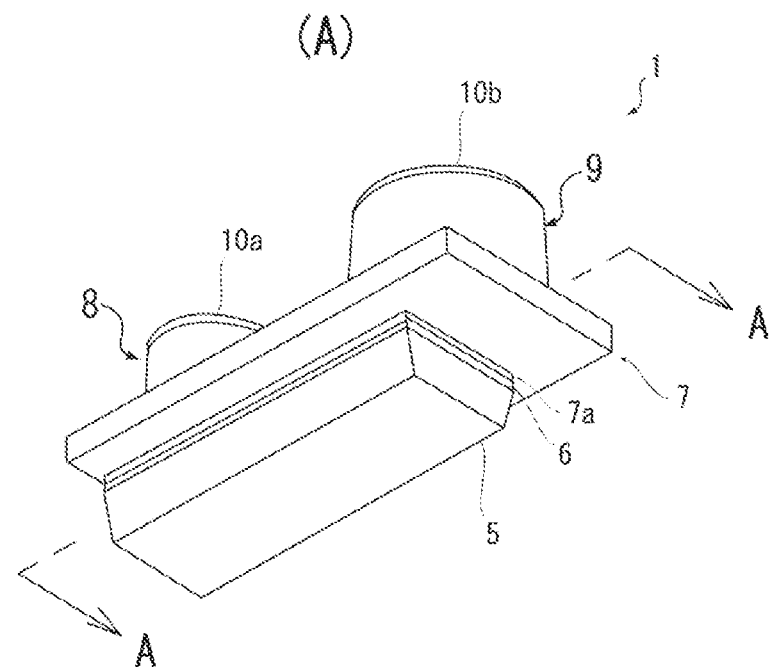
FIG. 2A is a perspective view of a sensor chip to be inserted in the immunoassay device of FIG. 1.
FIG. 2B is a view showing a section taken along the line A-A of FIG. 2A.
Figure 2:
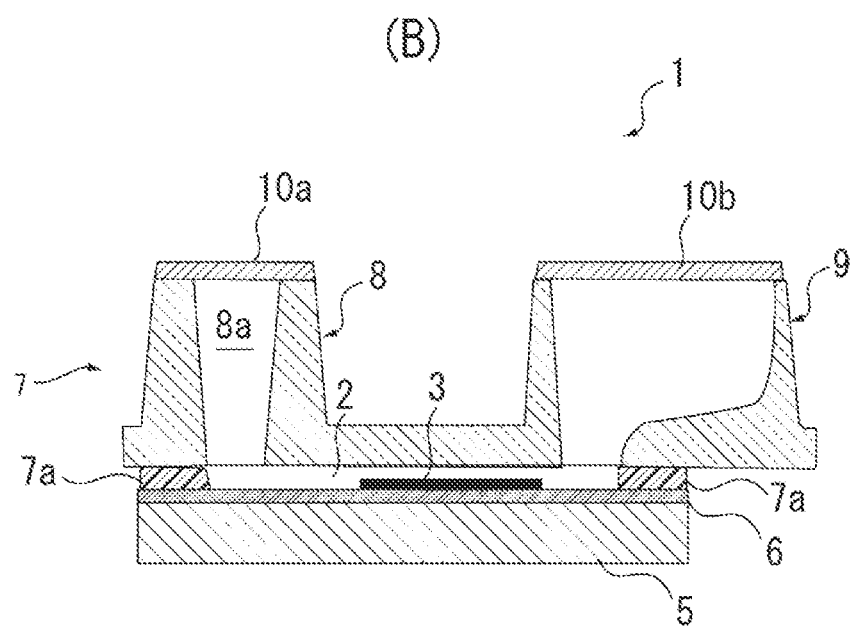

The inspection system 100 of the first embodiment includes: as illustrated in FIGS. 1 to 2, a sensor chip 1 that has a flow path 2 equipped with a reaction site 3 for a biological reaction in at least part of the flow path 2; and an SPFS device 4 as an inspection device where the sensor chip 1 is set and the above-described biological reaction is performed while performing the reciprocal liquid feeding for the flow path 2 and predetermined temperature adjustments (as will be described later), thereby detecting the biological reaction.

(Biological Reaction)

The above-described biological reaction refers to a biological reaction (e.g., immunological reaction) that is required for a medical diagnosis (pathological diagnosis). Examples of this biological reaction include: antigen-antibody reaction (biological reaction) between biomolecules specific to the blood of patients with malignant tumor, myocardial infarction, or the like (analytes; e.g., CTC, cardiac troponin I) and antibodies that specifically capture such biomolecules (ligands; e.g., CD45 antibody, Anti- Troponin I antibody, respectively corresponding to the above examples), as well as, antigen-antibody reaction (biological reaction) between biomolecules that are captured by the ligands and secondary antibodies that recognize epitopes of the biomolecules that are different from those recognized by the above antibodies and specifically bond with the biomolecules captured by the ligands.

[Sensor Chip]

First, the following will describe the configuration of the sensor chip 1. This sensor chip 1, as illustrated in FIG. 2, at least includes a dielectric member 5, a metallic thin film 6 that is formed over the upper surface of the dielectric member 5; and a minute-flow-path constituting member 7 provided on the metallic thin film 6.

(Minute-Flow-Path Constituting Member)

The minute-flow-path constituting member 7 includes, as illustrated in FIGS. 2A and 2B, a liquid discharger/suction unit 8 (described later), a liquid mixing unit 9 (described later), and the like. A minute flow path 2 is formed by joining the lower surface of the minute-flow-path constituting member 7 with the upper surface of the metallic thin film 6 on the dielectric member 5 using a frame-like double-sided tape 7a (refer to FIG. 2B).

(Dielectric Member)

The material of the dielectric member 5 includes optically transparent insulating resin and glass. The material of the dielectric member 5 preferably is a resin with a refractive index of 1.4 to 1.6 and with small double refraction.

The shape of the dielectric member 5 is, for example, a pyramid shape, such as a hexahedron having a substantially trapezoidal cross section (truncated quadrangular pyramid), quadrangular pyramid, cone, triangular pyramid, polygonal pyramid, or a frustum, which can be formed by injection molding.

(Metallic Thin Film)

The metallic thin film 6 of the sensor chip 1 is preferably made of at least one kind of metals selected from a group consisting of gold, silver, aluminum, copper, and platinum, and can be formed on the surface of the dielectric member 5 by means of a sputtering method, evaporation method, electrolytic plating method, electroless plating method, or the like.

The thickness of the metallic thin film 6 is preferably 5 to 500 nm, and, from an aspect of electric field reinforcing effect, 20 to 70 nm when the material of the metallic thin film 6 is gold, silver, copper, or platinum; 10 to 50 nm when aluminum; and 10 to 70 nm when alloy of these metals.

As a method of fixing the minute-flow-path constituting member 7 on the metallic thin film 6, apart from the above-described fixing method using the double-sided tape 7a, other fixing methods such as heat fusing, ultrasonic welding, fixing using adhesives (provided that the fixing maintains a predetermined height of the flow path 2) are exemplified.

FIG. 2B shows a section view taken along the line A-A of the sensor chip 1 illustrated in FIG. 2A. The sensor chip 1, as illustrated in FIG. 2B, is equipped with a liquid discharger/suction unit 8 on the upstream side (left side in FIG. 2B) of the minute flow path 2 (also simply referred to as the "flow path") formed by the minute-flow-path constituting member 7 on the metallic thin film 6 and with a liquid mixing unit 9 on the downstream side thereof (right side in FIG. 2B). The liquid discharger/suction unit 8 has a space 8a that communicates with the flow path 2 of the sensor chip 1, as well as, capable of accommodating the tip end of the pipette tip (liquid holding section) 10 as will be described later The upper surfaces of the liquid discharger/suction unit 8 and the liquid mixing unit 9 are, as illustrated in FIG. 2, sealed by hermetic seals 10a, 10b, and a reaction liquid (a specimen liquid, cleaning liquid, fluorescent-labelled secondary antibody aqueous solution, or the like) can be supplied to the minute flow path 2 by breaking the hermetic seal 10a on the liquid discharger/suction unit 8 side with the tip end (refer to FIG. 5) of the pipette tip (described later) 10 attached to the pump 12 of the liquid feeder 11.

It should be noted that the hermetic seal 10b has a vent (air hole) necessary for feeding a reaction liquid to the flow path 2 (not shown). It should be noted that the liquid mixing unit 9 may instead has a vent (air hole). Alternatively, a vent (air hole) may be formed by breaking through the hermetic seal 10b with a pipette tip or the like (liquid holding section) of the liquid feeder in the SPFS device before feeding a reaction liquid.

The minute flow path 2 of the sensor chip 1 is provided with a reaction site 3 (also, referred to as a sensor unit) for an immunoassay reaction and the reaction site 3 has antibodies (ligands) immobilized thereon that specifically bond with specific antigens (analytes) included in a specimen liquid (not shown).

The method of immobilizing may include forming a SAM (Self Assembled Monolayer) on the upper surface of the metallic thin film 6 using commercially available SAM forming reagent (e.g., 10-carboxy-1-decanethiol) and causing a ligand solution including N-hydroxysuccinimide (NHS) to contact with the SAM so as to make bonds between the SAM and ligands, whereby ligands are immobilized on the reaction site 3 (not shown).

An alternative method includes causing the reducing terminals of hydrophilic macromolecules, such as carboxymethyldextran (CMD), and the amino group of the SAM to form Schiff base bonding so as to immobilize the hydrophilic macromolecules on the SAM, dipping the area of the metallic thin film 6 including the immobilized portion in N-hydroxysuccinimide and water-soluble carbodiimide of 50 mM (mol m$^{-3}$) to 100 mM (mol m$^{-3}$), then, bringing the ligand (e.g., antibody) solution into contact with the above-described area to immobilize the ligands (e.g., antibodies) on the hydrophilic macromolecules (e.g., CMD), thereby immobilizing the ligands on the metallic thin film 6 via the hydrophilic macromolecules and SAM.

[SPFS Device]

Next, the configuration of the SPFS device 4 will be described. This SPFS device 4 is a surface plasmon fluorometric analysis device that detects analytes included in a specimen liquid utilizing a surface plasmon resonance (SPR) phenomenon.

Figure 3:
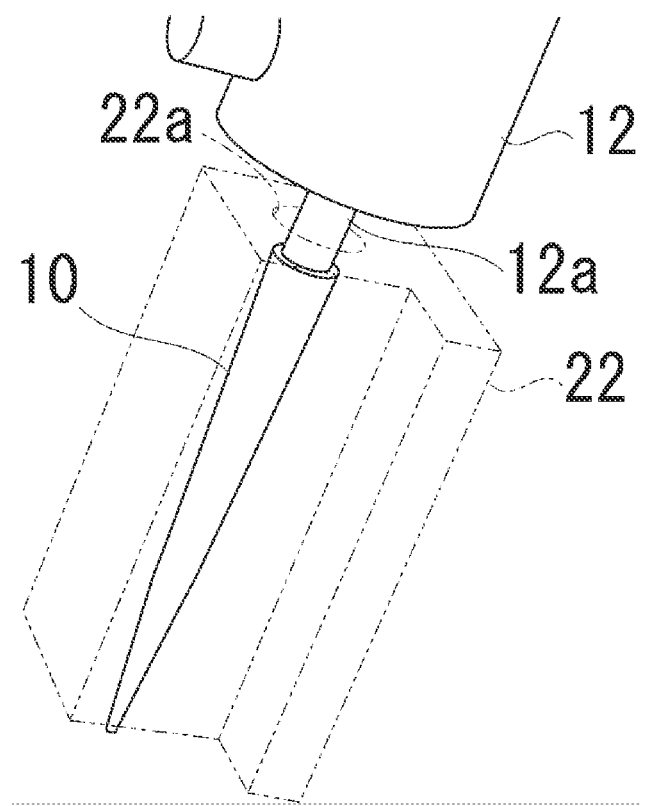
FIG. 3 is a partially enlarged view of a liquid feeder of the inspection system according to the first embodiment of FIG. 1.

The SPFS device 4, as illustrated in FIG. 1, at least includes a liquid feeder 11 that at least has a pump 12 and a pipette tip 10 as a liquid holding section; a first heat block (first temperature adjuster) 21 that adjusts the temperature of a reaction liquid (a specimen liquid, cleaning liquid, fluorescent-labelled secondary antibody solution, or a mixed solution thereof) that has flowed, by the liquid feeder 11, in the flow path 2 of the sensor chip 1; a second heat block (second temperature adjuster) 22 that adjusts the temperature of liquid held in the pipette tip 10 through temperature adjustment of the pipette tip 10 of the liquid feeder 11 (refer to FIG. 3).

Further, the SPFS device 4, as illustrated in FIG. 1, has a third heat block (third temperature adjuster) 23 that adjusts the temperature of the liquid reservoir 13 for reserving the reaction liquid and of the reaction liquid (e.g., specimen liquid) reserved in the liquid reservoir 13 before liquid-feeding. It should be noted that the above-described liquid feeder 11 of the SPFS device 4 and the first to third heat blocks 21 to 23 are arranged inside a case 14 that is provided in the SPFS device as a liquid feed reaction chamber.

It should be noted that this case 14 is preferably made of a heat-insulating resin. For example, the case 14 is preferably made of polystyrene form, rigid urethane foam, highly foamed polyethylene, or phenol form.

Further, the SPFS device 4 has: a sensor chip conveyance mechanism 15 that conveys the sensor chip 1 that is set by a user in the SPFS device 4 to a predetermined position inside the SPFS device 4 (a liquid feed reaction position RP of the case 14 or an optical detectable position DP of the optical measurement chamber (described later)); a light-emitting optical system 16 that emits excitation light h to the sensor chip 1 that has been conveyed to and arranged at the optical detectable position DP; and a light-receiving optical system 17 that receives fluorescent light that is emitted, in response to the excitation light h, from the sensor chip 1.

It should be noted that the above-described light-emitting optical system 16 and light-receiving optical system 17 of the SPFS device 4 are arranged inside a case 18 equipped in the SPFS device as an optical measurement chamber that is different from the above-described case. The case 18 is preferably made of a heat-insulating resin material. For example, the case 18 is preferably made of polystyrene form, rigid urethane foam, highly foamed polyethylene, or phenol form. Further, a heat-insulating material that is used for a partitioning member, as will be described later, may be used.

The case 14 as a liquid feed reaction chamber of the SPFS device 4 and the case 18 as an optical measurement chamber of the SPFS device 4, as illustrated in FIG. 1, are partitioned in an openable/closable manner by a partition 19 (described later) that opens/closes an opening through which both chambers communicate with each other, where both chambers are insulated from each other by closing the opening by the partition 19.

The SPFS device 4 has: a controller 24A that controls the operation of the above-described liquid feeder 11, first to third heat blocks 21 to 23, light-emitting optical system 16, light-receiving optical system 17, partition 19, and the like; and a memory 24B and the like used by the controller 24A.

[Liquid Feeder]

The liquid feeder 11 causes a reaction liquid to flow in and to flow out of the flow path 2 of the sensor chip 1, thus, has a pump 12 for feeding or sucking the reaction liquid to and from the flow path 2 of the sensor chip 1 and a pipette tip (liquid holding section) 10 attached to the pump 12. With the pipette tip 10 attached to the pump 12, suction and discharge operation of the pump 12 causes the pipette tip 10 to suck a liquid (e.g., a reaction liquid) and discharge the sucked liquid. The pump 12 may be, for example, a plunger pump or a micro pump described in Re-publication of PCT International Publication No. 2012/153723.

The liquid feeder 11 has a function of sucking a reaction liquid reserved in the liquid reservoir 13 by the pump 12 and holding it in the pipette tip 10, then, discharging the liquid held inside (by breaking the hermetic seal 10a of the liquid discharger/suction unit 8 side of the sensor chip 1) to cause the reaction liquid (e.g., a specimen liquid) to flow in the flow path 2 of the sensor chip 1.

The liquid feeder 11 further has a function of feeding a liquid (reciprocal liquid feeding) where at least some of the reaction liquid that has flowed in the flow path 2 of the sensor chip 1 is caused to flow out of the flow path 2 (in some cases, out of the sensor chip) and (after temporarily holding the liquid in the pipette tip 10) to flow in the flow path 2 again, thereby moving the liquid reciprocally, for a predetermined number of times.

The material of the pipette tip 10 may be the same material as pipette tips that are usually used in biotechnology experiments (e.g., polypropylene resin (PP), polystyrene (PS), polyethylene (PE), low density polyethylene (LDPE), fluororesin), or other material (e.g., resin, metal, or the like of higher heat conductivity than PP and other materials) that is heat conductive so that the warm or cold heat from the second heat block 22 can be easily conducted to the reaction liquid that is held in the pipette tip 10 through the thick part of the pipette tip 10.

The liquid holding section of the liquid feeder 11 may be, for example, a (flexible) capillary similar to those used in a capillary sequencer for decoding DNA sequences or a permanent nozzle made of metal, without limited to the above-described pipette tip.

[First Heat Block (First Temperature Adjuster)]

The first heat block (first temperature adjuster) 21 adjusts the temperature of the reaction liquid (e.g., a specimen liquid or a chemical liquid) that has flowed into the flow path 2 of the sensor chip 1 to a predetermined temperature (first temperature adjustment). The predetermined temperature is preferably set to an optimal temperature for a biological reaction that takes place at the reaction site 3 inside the sensor chip 1.

For example, when the biological reaction is antigen-antibody reaction between ligands immobilized on the reaction site and analytes relating to a disease included in a specimen liquid, the temperature of the liquid in the flow path 2 of the sensor chip 1 (especially, the reaction site 3) is set to the above-described predetermined temperature so that the highest efficiency can be attained in this biological reaction.

As illustrated in FIG. 1, the first heat block 21 is preferably provided adjacent to the sensor chip 1 and configured to adjust the temperature of the reaction site 3 of the sensor chip 1 in response to instructions from the controller 24A.

It should be noted that, instead of the heat block, the first temperature adjuster may be other known temperature adjustment means that can adjust the temperature of the reaction site 3 of the sensor chip 1 to the above-described predetermined temperature (first temperature adjustment). For example, the first temperature adjuster may be a blowing means that blows out cold or warm air toward the sensor chip 1 to make the temperature of the reaction liquid at the reaction site 3 the above-described predetermined temperature.

[Second Heat Block (Second Temperature Adjuster)]

The second heat block (second temperature adjuster) 22 (refer to FIGS. 1 and 3) adjusts the temperature of a reaction liquid (e.g., a specimen liquid or a chemical liquid) that is sucked from and discharged in (reciprocal liquid feeding) the flow path 2 of the sensor chip 1 by the liquid feeder 11 (second temperature adjustment) and at least adjusts the temperature of the reaction liquid that has flowed out of the flow path 2 of the sensor chip 1 in the reciprocal liquid feeding to maintain as much as possible at the temperature inside the flow path 2 before flowing out thereof.

Figure 7A:
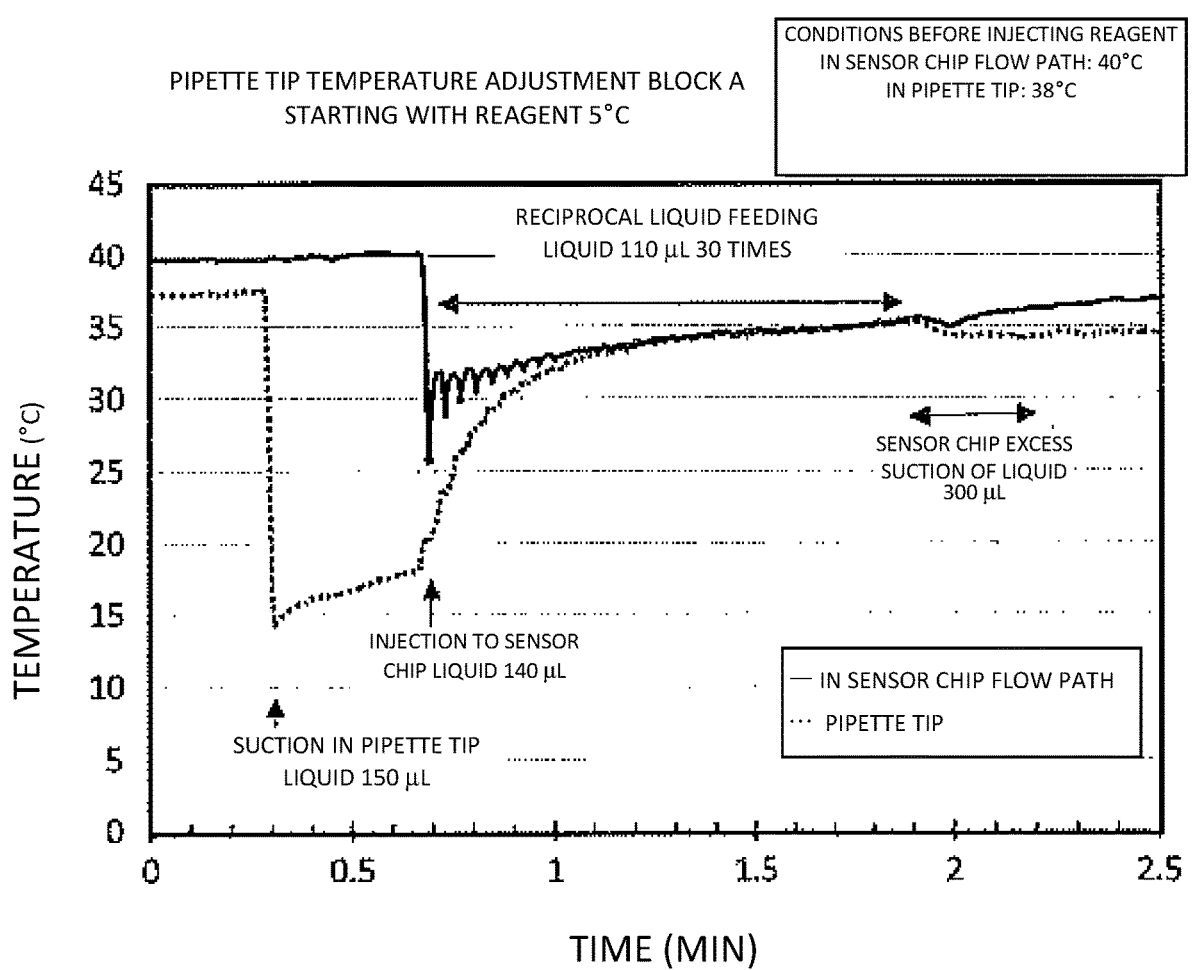
FIG. 7A is a view showing temperature change of a specimen liquid over time at different places (in a sensor chip flow path, in a pipette tip) of Example 1.
Figure 7B:
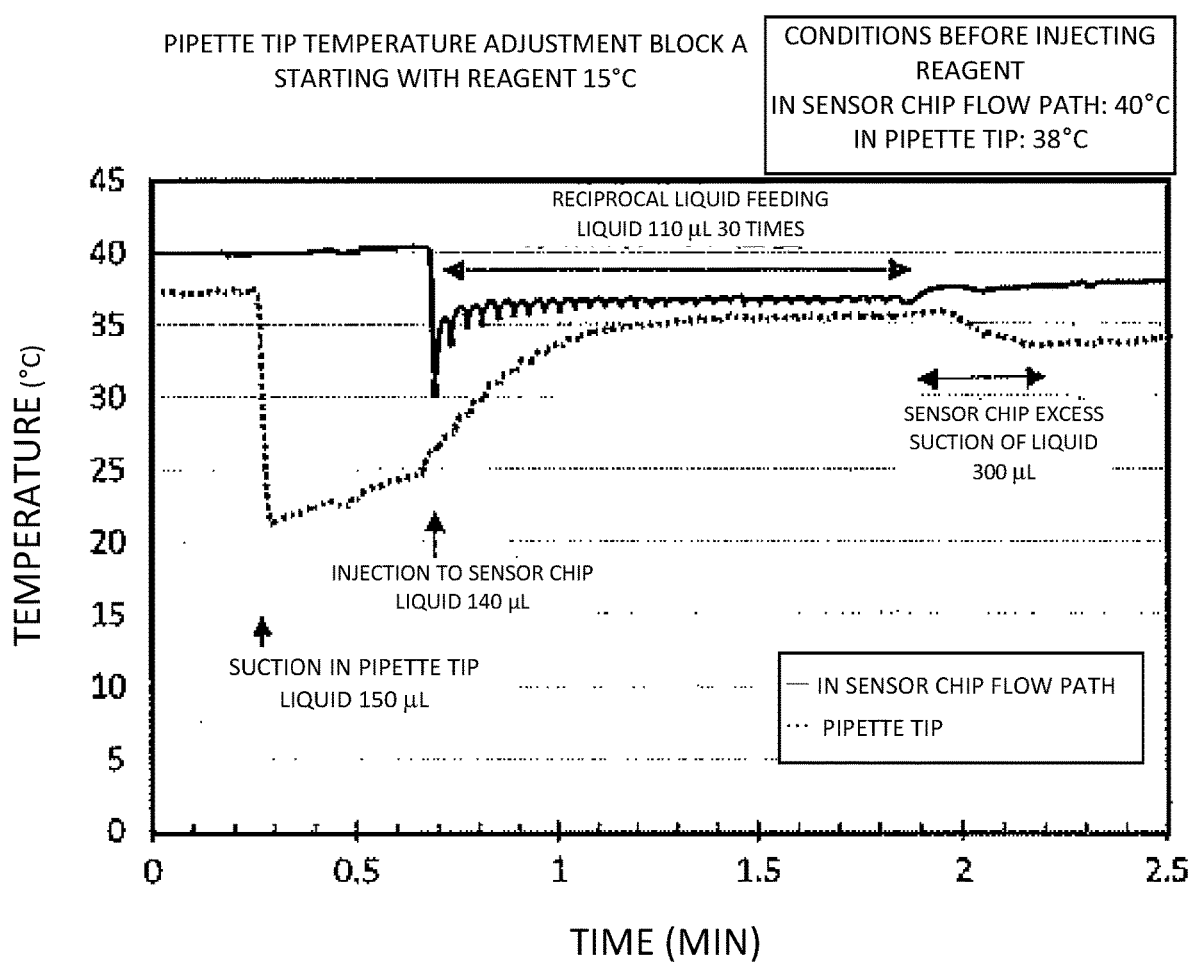
FIG. 7B is a view showing temperature change of a specimen liquid over time at different places in Example 2.
Figure 7C:
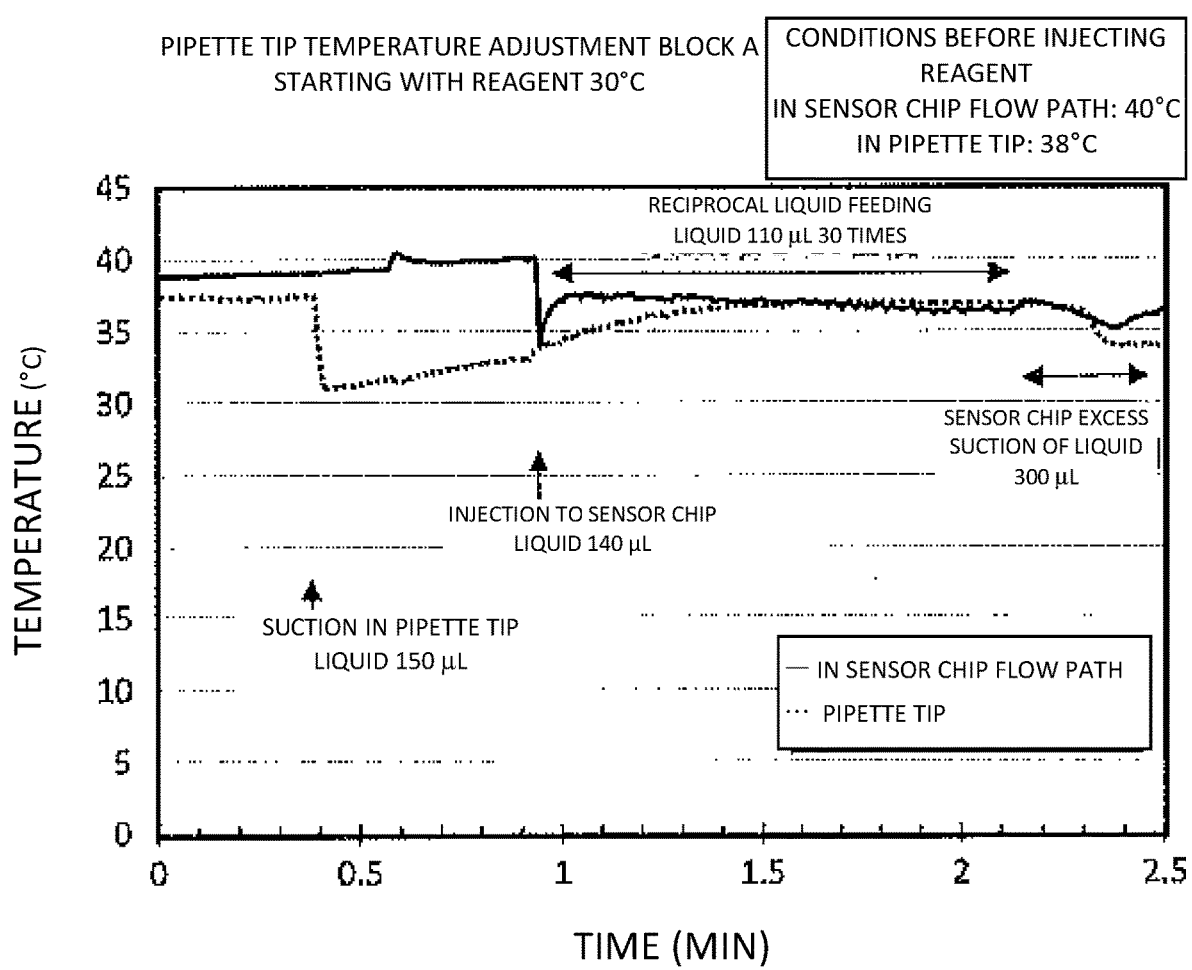
FIG. 7C is a view showing temperature change of a specimen liquid over time at different places in Example 3.
Figure 7D:
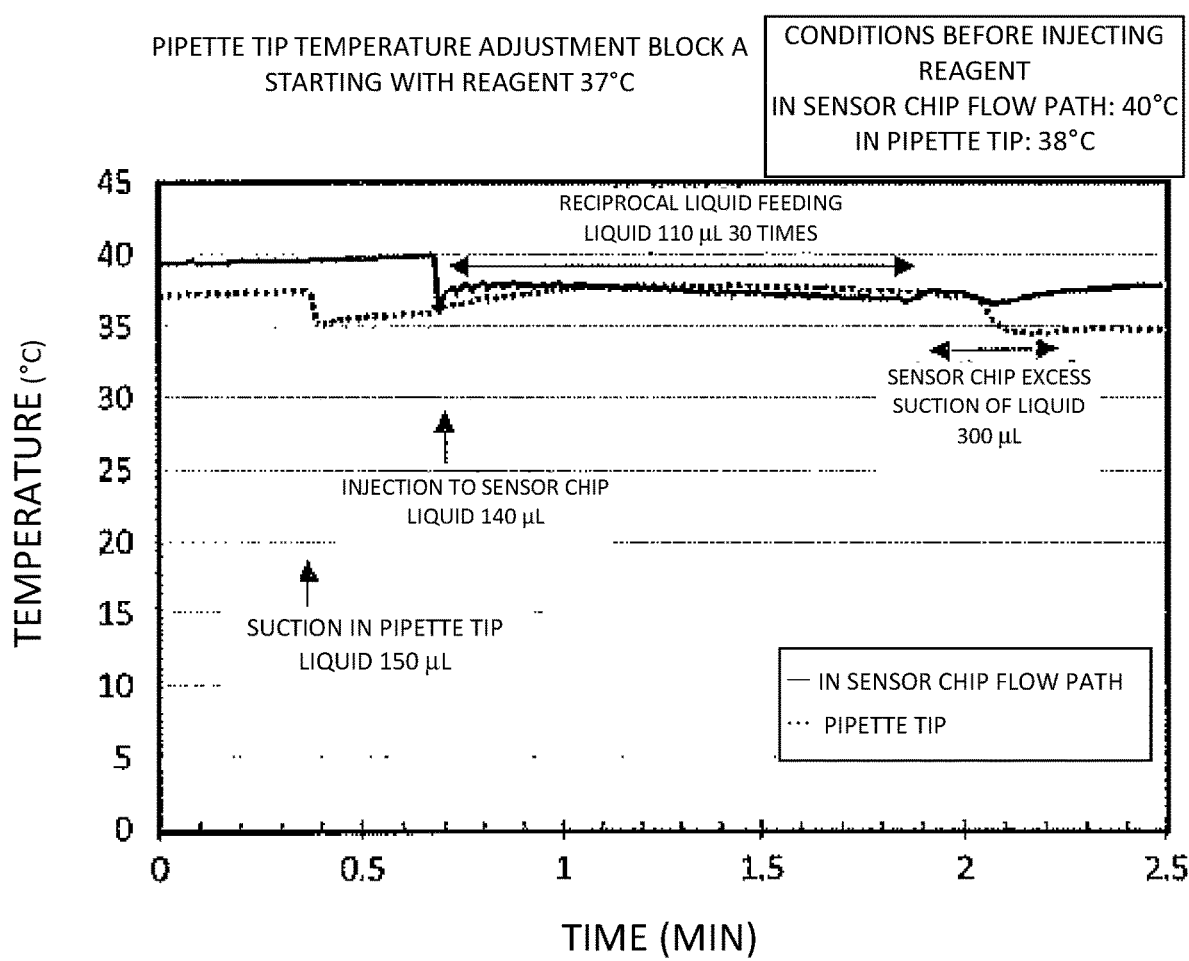
FIG. 7D is a view showing temperature change of a specimen liquid over time at different places in Example 4.
Figure 8A:
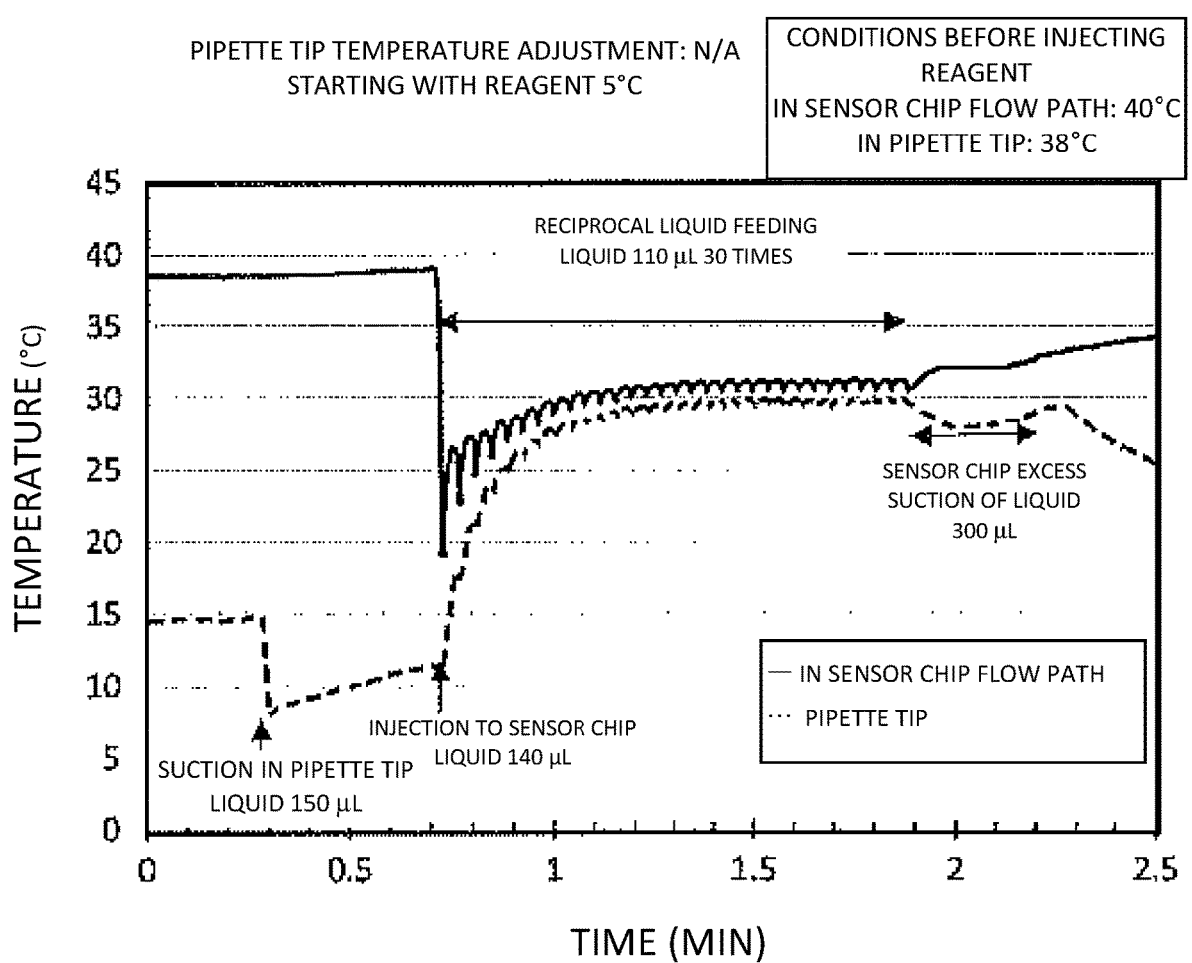
FIG. 8A is a view showing temperature change of a specimen liquid over time at different places in comparative Example 1.

Here, "adjust temperature to maintain as much as possible" means adjusting the temperature of the reaction liquid by the second temperature adjuster to make the fluctuation of the temperature of the reaction liquid during a single round of reciprocal liquid feeding (where a single peak appears in a chronological chart representing the temperature) (refer to FIGS. 7 and 8) becomes smaller than when reciprocal liquid feeding is performed under the same conditions without the second temperature adjustment (e.g., refer to FIGS. 7A and 8A in comparison).

In a specific example, during a biological reaction (e.g., antigen antibody reaction) while reciprocal liquid feeding of a specimen liquid including analytes is performed by the liquid feeder 11 at the reaction site 3 in the sensor chip 1 where ligands are immobilized, the second heat block 22 has a function of adjusting the temperature of the specimen liquid, which is temporarily transferred inside the pipette tip (liquid holding section) 10 of the liquid feeder 11 from the flow path 2 of the sensor chip 1 in the reciprocal liquid feeding, to maintain as much as possible at the temperature of the specimen liquid inside the flow path 2 of the sensor chip 1 before transferring the liquid to the pipette tip 10 by heating or cooling the pipette tip 10 by the second heat block 22.

FIG. 3 shows a partially enlarged perspective view showing the second heat block (second temperature adjuster) 22 and liquid feeder 11. As illustrated in FIG. 3, the pipette tip (liquid holding section) 10 of the liquid feeder 11 is covered over the (generally) entire peripheral surface with the second heat block 22.

In the specific example of FIG. 3, a resin (e.g., PP) pipette tip 10 is detachably attached to the pipette tip attachment base 12*a* of a cylindrical shape that is equipped on the pump 12 of the liquid feeder 11, and these pipette tip 10 and pipette tip attachment base 12*a* are inserted in a through hole (a tunnel section) 22*a* of a cylindrical shape formed in the second heat block 22 with a gap from the inner peripheral surface of the through hole 22*a*, thereby the (generally) entire periphery of the pipette tip 10 is covered with the second heat block 22. It should be noted that the second heat block 22 is fixed to the SPFS device 4 by means of a fixing means which is not shown.

The gap between the pipette tip 10 and the inner peripheral surface of the tunnel section 22*a* is to allow the liquid feeder 11 and second heat block 22 move relative to each other by an actuator (not shown) so that the tip end of the pipette tip 10 projects from the lower end opening of the tunnel section 22*a* or the pipette tip 10 is withdrawn from the lower end opening of the tunnel section 22*a*, whereby the hermetic seal 10*a* of the liquid discharger/suction unit 8 of the sensor chip 1 is broken through to allow liquid feeding. With this configuration, the pipette tip is replaceable after each inspection.

As for the second temperature adjuster, other known temperature adjustment means that can perform the second temperature adjustment to a reaction liquid inside the pipette tip (liquid holding section), for example, an air conditioning means that can control the air temperature inside the liquid feed reaction chamber, may also be used instead of the heat block. However, the configuration of having a heat block is preferable since a heat block can perform the second temperature adjustment with lower costs compared with such an air conditioning means.

Further, if a metallic permanent nozzle is provided as a liquid holding section instead of the pipette tip, a heater may be arranged as a second temperature adjuster outside the permanent nozzle and the heater may adjust the temperature of the permanent nozzle (second temperature adjustment).

[Liquid Reservoir]

The liquid reservoir 13 is for reserving, mixing, and draining a reaction liquid, and usually, there are preferably a plurality of kinds of liquid reservoirs for a variety of liquids as described above. Further the plurality of kinds of liquid reservoirs 13 are preferably linearly provided adjacent to the sensor chip 1 so that the liquid feeder 11 moves the shortest distance when it moves back and forth between the liquid discharger/suction unit 8 of the sensor chip 1 and each liquid reservoir 13.

The material of the liquid reservoir 13 is usually a synthetic resin, such as polypropylene and polyethylene, or glass, however, other material may also be used to enhance efficiency of the third temperature adjustment as will be described later (e.g., chemical-resistant fluororesin coating resin with high thermal conductivity, metal such as stainless steel).

[Third Heat Block (Third Temperature Adjuster)]

The third heat block (third temperature adjuster) 23 is a means to adjust the temperature of a reaction liquid reserved in the liquid reservoir 13 before liquid-feeding (third temperature adjustment) and performs temperature adjustment so that the reaction liquid of a predetermined temperature can be fed to the reaction site 3. The third temperature adjustment preferably adjusts the temperature of the reaction liquid inside the liquid reservoir 13 before liquid-feeding to the preset temperature targeted by the first temperature adjustment. The third temperature adjustment is usually performed via heating or cooling of the liquid reservoir 13.

The third heat block 23, as illustrated in FIG. 1, is preferably configured with a plurality of recessed portions corresponding to the shape of the bottoms of the plurality of liquid reservoirs 13 which are fitted into the recessed portions to be subjected to the third temperature adjustment.

As for the third temperature adjuster, other known temperature adjustment means can be used instead of the above-described heat block. For example, a blowing means that blows warm or cold air to the bottom of the liquid reservoir 13 from the lower part of the liquid reservoir 13 for the third temperature adjustment may be used.

[Light-Emitting Optical System]

Similar to conventional SPFS devices, the light-emitting optical system 16 includes, for example as illustrated in FIG. 1, a light source 25, an angle scanning mechanism 26 for adjusting the irradiation angle of the light source 25, and an optical control mechanism 27 for controlling the light source 25 to adjust the intensity or the like of excitation light emitted from the light source 25. The light source 25 may be a laser output device that can emit a laser beam of a wavelength of excitation light. The light-emitting optical system 16 has a function of emitting excitation light to the incident surface of the dielectric member 5 of the sensor chip 1 that is conveyed to a predetermined optical detectable position DP, causing the excitation light passing through inside of the dielectric member 5 to proceed towards, with predetermined incident angle θ which is a total internal reflection condition, the reaction site (sensor portion) 3 on the metallic thin film 6 having the reaction site (sensor portion) 3 on the upper surface, thereby causing the surface of the metallic thin film 6 to emit evanescent waves to excite the fluorescent material present at the reaction site (sensor portion) 3 in the minute flow path 2 of the sensor chip 1.

[Light-Receiving Optical System]

The light-receiving optical system 17 is an optical system that has the same configuration as the conventional SPFS device, and, as illustrated in FIG. 1, has, for example, a group of optical lenses 28, an excitation light cut filter for cutting components of excitation light (not shown), a light detector 29 for receiving and detecting fluorescent light, a sensor control mechanism 30 for controlling operation of the light detector 29, and a position switching mechanism (not shown) for locating the excitation light cut filter at the light axis of the group of optical lenses or moving the filter away from the light axis.

[Partition]

The partition 19, as described above, is a means for partitioning, in an openable/closable manner, the opening 20 that makes the case 14 as the liquid feed reaction chamber and the case 18 as the optical measurement chamber to communicate with each other. The partition 19 at least has a partitioning member 19a that advances/retracts relative to the opening 20 that makes the case 14 and case 18 to communicate with each other to close/open the opening 20. This partitioning member 19a is preferably made of a heat-insulating material. As for examples of the heat-insulating material, heat-insulating materials disclosed in Japanese Unexamined Patent Application Publication No. 2012-188323 and No. 2012-144394, heat-insulating materials using heat-insulating sheets disclosed in Japanese Unexamined Patent Application Publication No. 2012-102204 and No. 2012-062341, and commercially available heat insulating resin plates can be appropriately used.

It should be noted that the partition 19 has an actuator (not shown) and is configured to advance and retract the partitioning member 19a relative to the opening 20 by control of the controller 24A.

[Sensor Chip Conveyance Mechanism]

The sensor chip conveyance mechanism 15 (refer to FIG. 1) is a known means that allows a user to move the sensor chip 1 set in the SPFS device 4 to a predetermined position. The sensor chip conveyance mechanism 15 has a function of moving the sensor chip 1 to a liquid feed reaction position RP in the case 14 where the sensor chip 1 is subjected to liquid feeding and of moving the sensor chip 1 after completing a biological reaction to an optical detectable position DP in the case 18.

<<Immunoassay>>

Figure 6:
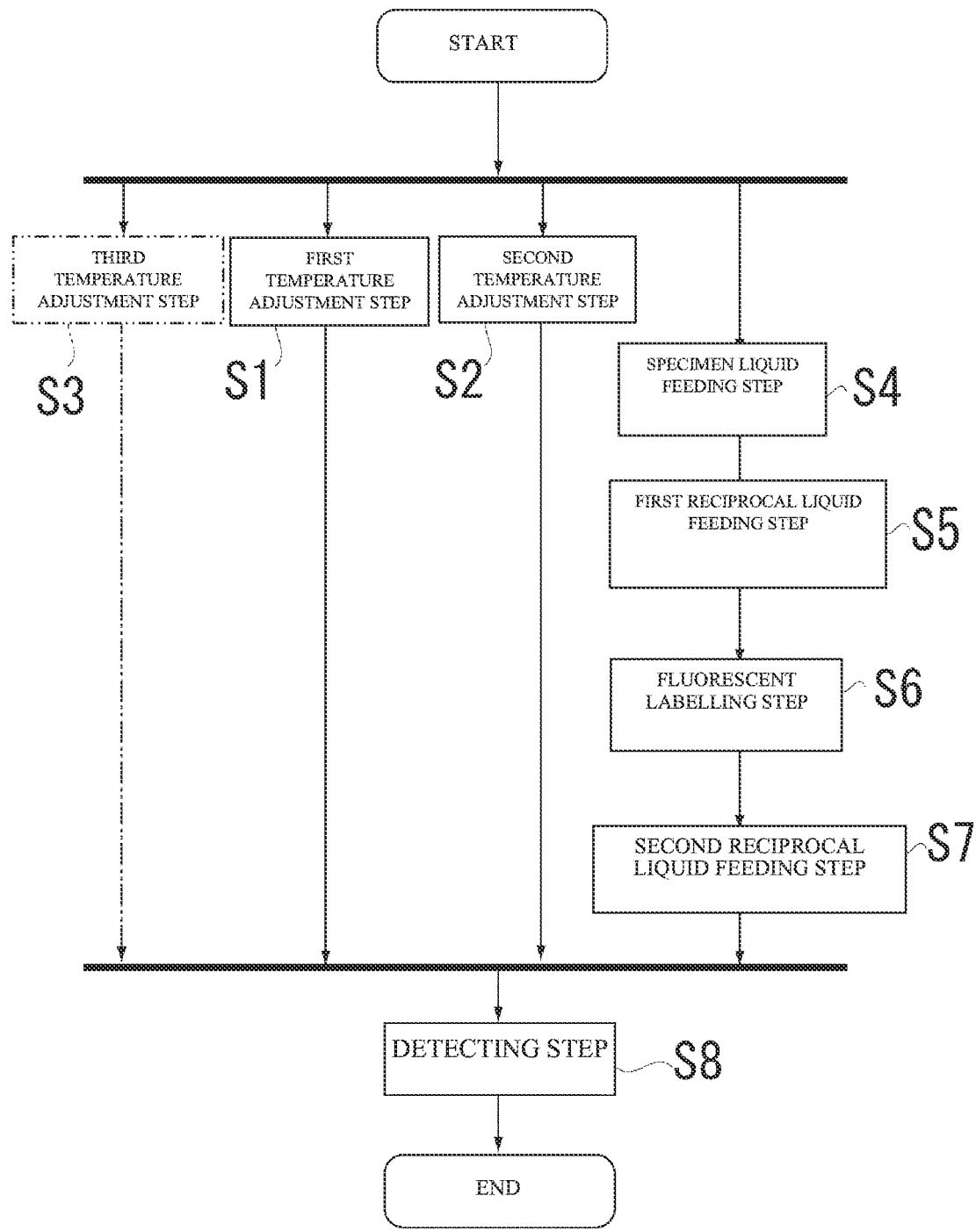
FIG. 6 is an immunoassay flowchart using the inspection system of the first embodiment, in which a two-dot-and-dash line indicates an arbitrary process.

The following will describe an immunoassay (an inspection method) with the above-described temperature adjustments (first and second temperature adjustments (and third temperature adjustment in some cases)) and reciprocal liquid feeding, using the inspection system of the first embodiment (refer to FIG. 6).

This inspection method, as illustrated in FIG. 6, includes: a first temperature adjustment step (S1) that adjusts the temperature of a reaction liquid that has flowed in the flow path 2 of the sensor chip 1 to a predetermined temperature (first temperature adjustment); a specimen liquid feeding step (S4) that feeds a specimen liquid to the reaction site 3 in the flow path 2 of the sensor chip 1; a second temperature adjustment step (S2) that adjusts the temperature of the reaction liquid to be sucked from and discharged to, by the liquid feeder 11, the flow path 2 of the sensor chip 1 (reciprocal liquid feeding) (second temperature adjustment); a first reciprocal liquid feeding step (S5) that performs liquid feeding where at least some of the specimen liquid that has flowed in the flow path 2 is caused to flow out of the flow path 2 and to flow in again, thereby moving the liquid reciprocally (reciprocal liquid feeding); a fluorescent labelling step (S6) that feeds a liquid of secondary antibodies labelled with a fluorescent material to label the analytes captured by the first antibodies with fluorescent-labelled secondary antibodies; a second reciprocal liquid feeding step (S7) that performs liquid feeding where at least some of the solution of fluorescent-labelled secondary antibodies that has flowed in the flow path 2 is caused to flow out of the flow path 2 and to flow in again, thereby moving the liquid reciprocally (reciprocal liquid feeding); and a detecting step (S8) that detects specimen substances captured at the reaction site by SPFS. It should be noted that, as illustrated in FIG. 6, the third temperature adjustment step (S3) may also be performed (refer to a two-dot-and-dash line of FIG. 6).

The above-described specimen liquid is a solution including specimens taken from a patient and used for pathological diagnosis, which may contain analytes (target biomolecules, such as biomolecules specific to blood of patients with malignant tumor, myocardial infarction, or the like). "Analytes" are molecules or fragments of molecules that are specifically recognized by (or recognize) and bond with first ligands, where such "molecules" and "fragments of molecules" may include, for example, nucleic acids (single stranded or double stranded DNA, RNA, polynucleotide, oligonucleotide, PNA (peptide nucleic acid) and the like, or nucleosides, nucleotides and modified molecules thereof), proteins (e.g., polypeptide, oligopeptide), amino acids (including modified amino acids), saccharides (e.g., oligosaccharides, polysaccharides, sugar chains), lipids, or modified molecules or complexes of these, specifically, for example, AFP [a fetoprotein] and other carcinoembryonic antigens and tumor markers, signaling substances, and hormones, without limitation.

[First Temperature Adjustment Step]

The first temperature adjustment step (S1) is a step of performing a first temperature adjustment by the first heat block (first temperature adjuster) 21. The first temperature adjustment step (S1) is preferably performed at least from the specimen liquid feeding step (S4) until the end of the second reciprocal liquid feeding step (S7) (refer to FIG. 6). The temperature at the reaction site 3 of the sensor chip 1 is adjusted to a predetermined temperature (e.g., a temperature suitable for a biological reaction) by the first heat block 21 provided adjacent to the sensor chip 1 in response to instructions from the controller 24A.

Further, the first temperature adjustment step (S1) is preferably performed before the start of the specimen liquid feeding step (S4) for a time duration required for a temperature surrounding the reaction site 3 of the sensor chip 1 to reach the target temperature value of the first temperature adjustment.

[Second Temperature Adjustment Step]

The second temperature adjustment step (S2) is a step of performing a second temperature adjustment by the second heat block (second temperature adjuster) 22, which is performed, as described above, at least along with the reciprocal liquid feeding (the first reciprocal liquid feeding step (S5) and the second reciprocal liquid feeding step (S7)) (refer to FIG. 6). The second heat block 22 provided adjacent to the pipette tip 10 is maintained at a certain temperature in response to instructions from the controller 24A to adjust the temperature of the reaction liquid when the reaction liquid has flowed out of the sensor chip 1 (sucked in the pipette tip 10) so that the reaction liquid is not easily affected by the temperature inside the SPFS device. The second temperature adjustment step (S2) is preferably performed at least from any time before the specimen liquid is fed to the sensor chip 1 until time when the biological reaction (in this example, the second reciprocal liquid feeding step (S7)) ends.

[Third Temperature Adjustment Step]

The third temperature adjustment step (S3) is a step of adjusting the temperature, by the third heat block (third temperature adjuster) 23, of a reaction liquid (e.g., a specimen liquid, a cleaning liquid, and/or a fluorescent-labelled secondary antibody solution) reserved in the liquid reservoir 13 before liquid feeding (third temperature adjustment). The third temperature adjustment step (S3) adjusts the temperature of the reaction liquid that is reserved in the liquid reservoir 13 before being fed to the sensor chip 1 to a predetermined temperature (e.g., a temperature suitable for a biological reaction).

The third temperature adjustment step (S3) is an arbitrary step, which is performed during an arbitrary time (time duration) from arbitrary time before the start of the specimen liquid feeding step (S4) until time before the detecting step (S8), as will be described later. The third temperature adjustment step (S3) is preferably performed from time before the start of each step (i.e., the specimen liquid feeding step (S4), first reciprocal liquid feeding step (S5), or fluorescent labelling step (S6)) for a duration of time that is required for the temperature of each reaction liquid to reach a target temperature value of the first temperature adjustment. For example, the third temperature adjustment of the fluorescent-labelled secondary antibody solution used in the fluorescent labeling step (S6) is preferably performed from time before the start of the above-described fluorescent labeling step (S6) for a duration of time required for the temperature of the fluorescent-labelled secondary antibody solution to reach a target temperature value of the first temperature adjustment by the third temperature adjustment (until time when feeding of the fluorescent-labelled secondary antibody solution in the flow path of the sensor chip 1 ends).

It should be noted that, if a temperature suitable for antigen-antibody reaction (biological reaction) between the ligands immobilized on the reaction site 3 of the sensor chip 1 and the analytes in a specimen liquid is different from a temperature suitable for antigen-antibody reaction (biological reaction) between the analytes bonded with the ligands and fluorescent-labelled secondary antibodies, the target temperatures of the first to third temperature adjustments at the first to third temperature adjustment steps performed in parallel to the antibody liquid feeding step, reciprocal liquid feeding step, and fluorescent labeling step, as will be described later, may be set at temperatures suitable for respective biological reactions.

[Specimen Liquid Feeding Step]

The specimen liquid feeding step (S4) is a step of feeding a specimen liquid in the flow path 2 that includes the reaction site 3 of the sensor chip 1 to cause specimens (e.g., biomolecules for determining a disease) included in the specimen liquid to make a biological reaction with capturing bodies (substances that capture the specimens, e.g., antibodies specifically bond with the biomolecules) immobilized on the reaction site 3. As described above, it is preferable that the temperature of the flow path 2 including the reaction site 3 and the temperature of the pipette tip 10 become a target temperature (e.g., a temperature suitable for a biological reaction) through the first and second temperature adjustment steps by the time the specimen liquid feeding step (S4) starts.

[First Reciprocal Liquid Feeding Step]

The first reciprocal liquid feeding step (S5) is, as described above, a step of liquid feeding (reciprocal liquid feeding) by the liquid feeder 11 where at least some of the specimen liquid that has flowed in the flow path 2 including the reaction site 3 of the sensor chip 1 is caused to flow out of the flow path 2 of the sensor chip 1 and to flow in again, thereby moving the liquid reciprocally. With this reciprocal liquid feeding, the specimen liquid repeatedly flows over the reaction site 3 and the specimens in the specimen liquid (detection target biomolecules) are repeatedly exposed to collision with the ligands (e.g., antibodies) immobilized on the reaction site 3, thereby increasing the efficiency of a biological reaction occurring between the specimens (analytes such as biomolecules) and antibodies immobilized on the reaction site 3.

If from suction until discharge of the liquid feeder is counted as one reciprocal liquid feeding, the reciprocal liquid feeding is preferably performed 10 to 40 times in consideration of reaction efficiency and operability, which can be varied according to the reaction efficiency of a biological reaction.

After the reciprocal liquid feeding of a specimen liquid for a predetermined number of times, the liquid feeder 11 sucks the specimen liquid and disposes in a drainage container. Subsequently, a cleaning liquid is instilled on the liquid discharger/suction unit 8 of the sensor chip 1 and fed to the flow path 2 by the pump 12 of the liquid feeder 11 for cleaning to remove unreacting antigens that remain in the reaction site 3. The cleaning liquid may be a buffering solution, such as PBS, or water.

[Fluorescent Labelling Step]

The fluorescent labeling step (S6) is a step of feeding a fluorescent-labelled secondary antibody solution in the flow path 2 of the sensor chip 1 and making the specimens (analytes) that were bonded with the ligands (first antibodies) immobilized on the reaction site 3 of the flow path 2 bond with fluorescent-labelled secondary antibodies to fluorescent-label the analytes.

The fluorescent-labelled secondary antibody solution is a solution prepared by labelling secondary antibodies, which can bond with analytes in a specimen liquid bonded with the ligands immobilized on the reaction site 3 of the sensor chip 1, with a fluorescent material and dissolving the labelled secondary antibodies in a predetermined solvent (a buffering liquid such as PBS).

Common fluorescent dyes are typically used for the above-described fluorescent material, although semiconductor nanoparticles, fluorescent dyes, and other known fluorescent materials may instead be used. Further, fluorescent nanoparticle aggregates manufactured by a manufacturing method of wrapping up fluorescent dyes with resin or silica as abase (immobilizing a fluorescent material on the inside or outside surface of the base) (U.S. Pat. No. 5,326,692 (1992), Langmuir Vol. 8 p. 2921 (1992)) may also be used.

Examples of fluorescent dyes include fluorescent dyes of fluorescein family (Integrated DNA Technologies, Inc.), fluorescent dyes of polyhalofluorescein family (Applied Biosystems Japan Ltd.), fluorescent dyes of hexachlorofluorescein family (Applied Biosystems Japan Ltd.), fluorescent dyes of coumarin family (Invitrogen Japan K.K.), fluorescent dyes of rhodamine family (GE Healthcare Bioscience Co., Ltd.), fluorescent dyes of cyanine family, fluorescent dyes of indocathocyanine family, fluorescent dyes of oxazine family, fluorescent dyes of thiazine family, fluorescent dyes of squaraine family, fluorescent dyes of chelated lanthanide family, fluorescent dyes of BODIPY (registered trademark) family (Invitrogen Japan K.K.), fluorescent dyes of naphthalenesulfonic acid family, fluorescent dyes of pyrene family, fluorescent dyes of triphenylmethane family, and organic fluorescent dyes, such as Alexa Fluor (registered trademark) dye series (Invitrogen Japan K.K.).

[Second Reciprocal Liquid Feeding Step]

The second reciprocal liquid feeding step (S7) is, as described above, a step of liquid feeding (reciprocal liquid feeding) by the liquid feeder 11 where at least some of the fluorescent-labelled secondary antibody solution that has flowed in the flow path 2 including the reaction site 3 of the sensor chip 1 is caused to flow out of the flow path 2 of the sensor chip 1 and to flow in again the flow path 2, thereby moving the liquid reciprocally. With this reciprocal liquid feeding, the fluorescent-labelled secondary antibody solution repeatedly flows over the reaction site 3 and the fluorescent-labelled secondary antibodies in the solution are repeatedly exposed to collision with the analytes captured by the ligands at the reaction site 3, thereby increasing the efficiency of a biological reaction occurring between the specimens (analytes such as biomolecules) and the above-described secondary antibodies.

If from suction until discharge of the liquid feeder is counted as one reciprocal liquid feeding, the reciprocal liquid feeding is preferably performed 10 to 40 times in consideration of reaction efficiency and operability, which can be varied according to the reaction efficiency of a biological reaction.

After the reciprocal liquid feeding of the specimen liquid for a predetermined number of times, the liquid feeder 11 sucks the specimen liquid and disposes in a drainage container. Subsequently, a cleaning liquid is instilled on the liquid discharger/suction unit 8 of the sensor chip 1 and fed to the flow path 2 by the pump 12 of the liquid feeder 11 for cleaning to remove unreacting substances that remain in the reaction site 3. The cleaning liquid may be a buffering solution, such as PBS, or water.

[Detecting Step]

The detecting step (S8) is a step of using SPFS to excite the fluorescent material of the secondary antibodies bonded with the analytes captured by the ligands at the reaction site 3 of the sensor chip 1 and detecting the presence of specimens (analytes).

The SPFS is similar to common SPFS, which irradiates the metallic thin film 6 with excitation light, causing the metallic thin film 6 to generate evanescent waves that are amplified by surface plasmon resonances occurring in the metallic thin film, thereby exciting the fluorescent material to emit light.

It should be noted that, before the detecting step (S8), the following operations are performed: the partition 19 opens the opening 20, making the case 14 and the case 18 communicate with each other; the sensor chip conveyance mechanism 15 conveys the sensor chip 1 at the liquid feed reaction position RP of the case 14 to the optical detectable position DP of the case 18; then the opening 20 is closed immediately after the conveyance. This conveyance of the sensor chip is preferably performed within a very short time so that air within the case 14 that has changed by the first and second temperature adjustments (or first to third temperature adjustments) will not flow in the case 18.

The following will describe the effects of the inspection system according to the first embodiment.

(1) During the reciprocal liquid feeding, the second heat block (second temperature adjuster) 22 adjusts the temperature (through temperature adjustment of the pipette tip (liquid holding section) 10 of the liquid feeder 11) of a reaction liquid (a specimen liquid, a chemical liquid, or the like) that has flowed out of the flow path 2 of the sensor chip 1 so that the temperature of the reaction liquid (a specimen liquid, a chemical liquid, or the like) is maintained as much as possible at the temperature of the reaction liquid before flowing out of the flow path 2. Thus, even if reciprocal liquid feeding is performed with a difference in temperature between the reaction liquid at the reaction site 3 in the flow path 2 of the sensor chip 1 (central value) and the environment within the SPFS device (detecting device) 4 (for example, 5° C. or more difference), the temperature of the reaction liquid that is being reciprocally fed is stable without easily deviating from the target temperature of the reaction site (central value) (a temperature suitable for a biological reaction), i.e., without temperature fluctuation, thus, the efficiency of the biological reaction can be maintained. Moreover, the robustness of the inspection system for reaction liquids (a specimen liquid, a chemical liquid, and the like) with varying initial temperatures is improved.

(2) Since the entire periphery of the pipette tip (liquid holding section) 10 of the liquid feeder 11 is covered with the second heat block (second temperature adjuster) 22, the reaction liquid being reciprocally fed is hardly affected by the temperature change within the SPFS device 4, therefore, the temperature change is negligible.

(3) The third heat block (third temperature adjuster) 23 adjusts the temperature of a reaction liquid (a specimen liquid, a chemical liquid, or the like) in the liquid reservoir 13 to be fed in the flow path 2 of the sensor chip 1 to the same temperature as the first temperature adjustment by the first heat block (first temperature adjuster) 21, thus, even if the reaction liquid is fed to the flow path 2 and reciprocal feeding of the reaction liquid is performed, the temperature within the flow path 2 of the sensor chip 1 is not easily changed, stabilizing the temperature within the flow path 2.

(4) With the partition 19 that opens and closes the opening 20 that makes the case 14 as the liquid feed reaction chamber and the case 18 as the optical measurement chamber to communicate with each other, the opening 20 can be closed by the partition 19 during the biological reaction or optical measurement, narrowing the space (a space within the case 14), to which the sensor chip during a reaction is exposed, thereby facilitating stabilization of the temperature for the biological reaction by the first and second temperature adjustments (in some cases, the first to third temperature adjustments).

By preventing cold or warm air of the case 18 flowing in the case 14 during a biological reaction, the temperature of the environment surrounding the sensor chip 1 is not easily changed, and the biological reaction can be stabilized.

Further, upon optical measurement, the air in the case 14 as the liquid feed reaction chamber, which temperature has been raised by the first and second temperature adjustments (in some cases, the first to third temperature adjustments), does not easily flow in the case 18 as the optical measurement chamber, as the result, stabilizing the temperature at the light source 25 (e.g., laser irradiation device) inside the case 18 without largely deviating from a temperature suitable for the use of the light source 25, thus, stabilizing the function of the light source 25, as well as, advantageously extending the use life of the light source 25. Further, the use lives of sensors other than the light source 25 of the case 18 can also be extended.

(5) In the case of (4), if the temperature of the space in the case 18 is lower than the temperature of the space in the case 14 during a biological reaction, the effect of extending the use life as described in (4) can be advantageously obtained.

Second Embodiment

Figure 4:
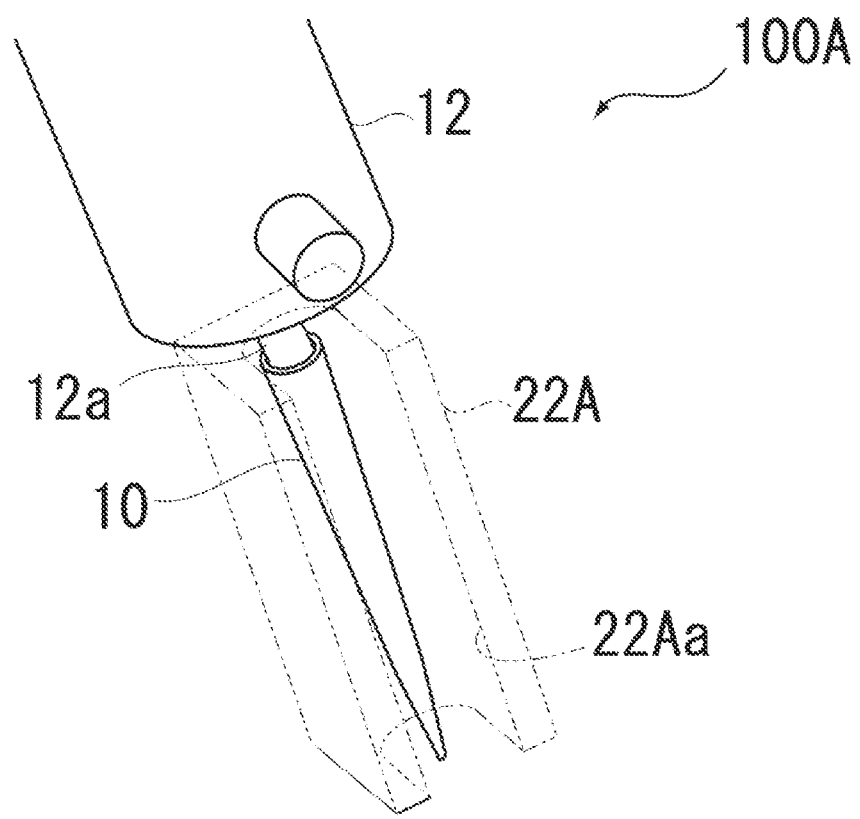
FIG. 4 is a view showing an inspection system of a second embodiment.

FIG. 4 illustrates the inspection system 100A of the second embodiment.

The inspection system 100A of the second embodiment is different from the inspection system 100 of the first embodiment, as illustrated in FIG. 4, in that the second heat block 22A of U-shaped section is provided along the longitudinal direction of the pipette tip 10 to surround the pipette tip 10 with a gap inbetween. In other words, the second heat block 22A is of a shape where one side wall of a cylindrical heat block of rectangular section is cut out and open (opening).

It should be noted that other components of the inspection system 100A are the same as the inspection system 100 of the first embodiment, thus, the drawings and description thereof are omitted.

According to the inspection system 100A of the second embodiment, the pipette tip 10 can be easily detached/attached in the SPFS device, which improves operability, shortens the inspection time, and improves throughput.

It should be noted that the pipette tip 10 of the liquid feeder 11 is required to be replaced with new pipette tip upon each inspection for preventing contamination of specimens. Thus, detaching and attaching operation of the pipette tip 10 is always included in each inspection process.

Further, according to the configuration of the inspection system 100A of the second embodiment, the movement of a liquid in the pipette tip 10 can be observed; for example, when the pump or the like fails, the occurring problem can be quickly detected, and the possibility of not obtaining a correct inspection result due to the biological reaction with inappropriate liquid feeding can be recognized.

It should be noted that the opening 22Aa of the second heat block 22A is not restricted to the opening shape of FIG. 4, as long as the opening shape can easily realize automatic detachment/attachment, in the device, of the pipette tip 10 that is attached to the pump 12 of the liquid feeder 11. For example, the shape of the opening 22Aa of the second heat block 22A may be of a shape where the opening 22Aa is tapered toward the tip end of the pipette tip 10 in accordance with the shape of the pipette tip 10 to improve heat insulating efficiency.

Third Embodiment

Figure 5:
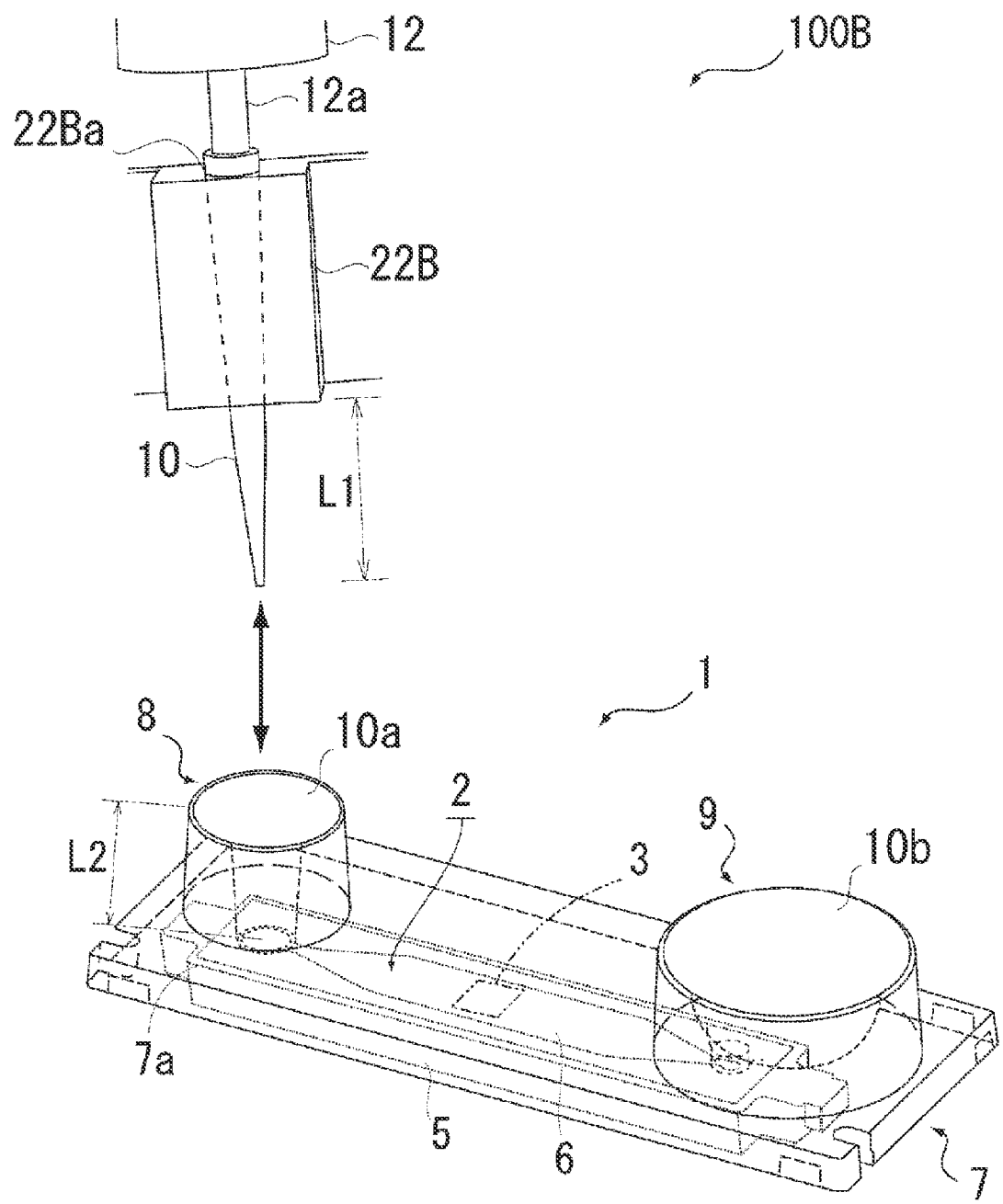
FIG. 5 is a view showing an inspection system of a third embodiment.

FIG. 5 illustrates the inspection system 100B of the third embodiment.

In the inspection system 100B of the third embodiment, as illustrated in FIG. 5, the second heat block 22B has a through hole 22Ba, through which the pipette tip 10 is inserted. Further, this pipette tip 10 is attached to the pipette tip attachment base 12a of the pump 12. In addition, only a part of the pipette tip 10 is covered with the second heat block 22B so that at least the tip end of the pipette tip 10 is exposed when the pipette tip 10 is inserted in the space 8a of the liquid discharger/suction unit 8 of the sensor chip 1.

When the length of the exposed tip end of the pipette tip 10 is defined as L1, and the depth of the space 8a of the liquid discharger/suction unit 8 of the sensor chip 1 is defined as L2 (refer to FIG. 5), L1 and L2 are set to be L1 L2. L1 and L2 are preferably generally the same lengths. It should be noted that the other components of the inspection system 100B are the same as the components of the inspection system 100 of the first embodiment, thus, the drawings and description thereof are omitted.

According to the inspection system 100B of the third embodiment, the pipette tip can be inserted until deep inside the space 8a of the sensor chip 1, thus, stabilizing liquid feeding.

EXAMPLES

The following will describe examples of the present invention using the inspection system of the first embodiment and comparative examples of a conventional inspection system that does not have the second temperature adjuster, with reference to FIGS. 7 to 8. It should be noted that the inspection systems used in the examples and comparative examples have thermistors in the flow path 2 of the sensor chip 1 and in the pipette tip 10 to monitor the temperature of a reaction liquid at each unit of the inspection system during, before, and after the reciprocal liquid feeding. Further, the temperature inside the SPFS device is adjusted to 15° C. before conducting the examples and comparative examples.

Example 1

First, the first heat block (first temperature adjuster) 21 adjusted the temperature inside the flow path 2 of the sensor chip 1 to 40° C. (first temperature adjustment), and the second heat block (second temperature adjuster) 22 heated the pipette tip (liquid holding section) 10 so as to adjust the pipette tip 10 and inside thereof to 38° C. (second temperature adjustment) (first and second temperature adjustment steps).

Next, the liquid feeder 11 sucked and held 150 μL of a specimen liquid of 5° C. from the liquid reservoir 13 (time T=0.3 minutes) and, while the tip end of the pipette tip 10 was being inserted inside (space 8a) the liquid discharger/suction unit 8 of the sensor chip 1, fed 140 μL of the held specimen liquid in the flow path 2 of the sensor chip 1 (time T=0.7) (specimen liquid feeding step).

By counting, as one reciprocal liquid feeding, the operation where the liquid feeder 11 sucked and held, in the pipette tip 10, 110 μL out of 150 μL specimen liquid in the flow path 2 of the sensor chip 1 and discharged (flowed out the liquid) in the flow path 2 while the tip end of the pipette tip 10 was being inserted inside the space 8a of the liquid discharger/suction unit 8 of the sensor chip 1, the reciprocal liquid feeding was repeated 30 times (time T=0.7 to 1.8) (first reciprocal liquid feeding step). It should be noted that, after the first reciprocal liquid feeding step, processing of cleaning the flow path 2 of the sensor chip 1 was performed using a PBS buffering solution.

Next, the liquid feeder 11 sucked 300 μL specimen liquid, which is excess amount compared with the fed specimen liquid, from the flow path 2 of the sensor chip 1 to remove the specimen liquid of the sensor chip 1, then, the fluorescent labeling step, the second reciprocal liquid feeding step (including the above cleaning processing), and the detecting step were performed (not shown). FIG. 7A shows a chart representing the temperature change of each unit (inside the flow path of the sensor chip, inside the pipette tip) monitored over time in Example 1.

It should be noted that, in Example 1, a temperature adjustment by the second temperature adjuster was performed for: the cleaning liquid that was fed to the flow path of the sensor chip in the cleaning processing that was performed after the first reciprocal liquid feeding step; the fluorescent-labelled secondary antibodies that were fed (or reciprocally fed) to the flow path of the sensor chip at the fluorescent labeling step and the second reciprocal liquid feeding step; and the cleaning liquid that was fed to the flow path of the sensor chip in cleaning processing performed after the second reciprocal liquid feeding step (which is similarly done in other examples as well).

Example 2

In Example 1, the steps were performed in the same way as Example 1 except that the temperature of the specimen liquid for feeding was set to 15° C. The resultant chart is shown in FIG. 7B.

Example 3

In Example 1, the steps were performed in the same way as Example 1 except that the temperature of the specimen liquid for feeding was set to 30° C. The resultant chart is shown in FIG. 7C.

Example 4

In Example 1, the steps were performed in the same way as Example 1 except that the temperature of the specimen liquid for feeding was set to 37° C. The resultant chart is shown in FIG. 7D.

Comparative Example 1

The steps were performed in the same way as Example 1 except that the second heat block was removed from the system that was used in Example 1 and, thus, the second temperature adjustment (step) was not performed. The result is shown in FIG. 8A. It should be noted that the temperature inside the sensor chip was 39° C., which is generally the same temperature as in Examples 1 to 4 and is within a detection error.

Comparative Example 2

Figure 8B:
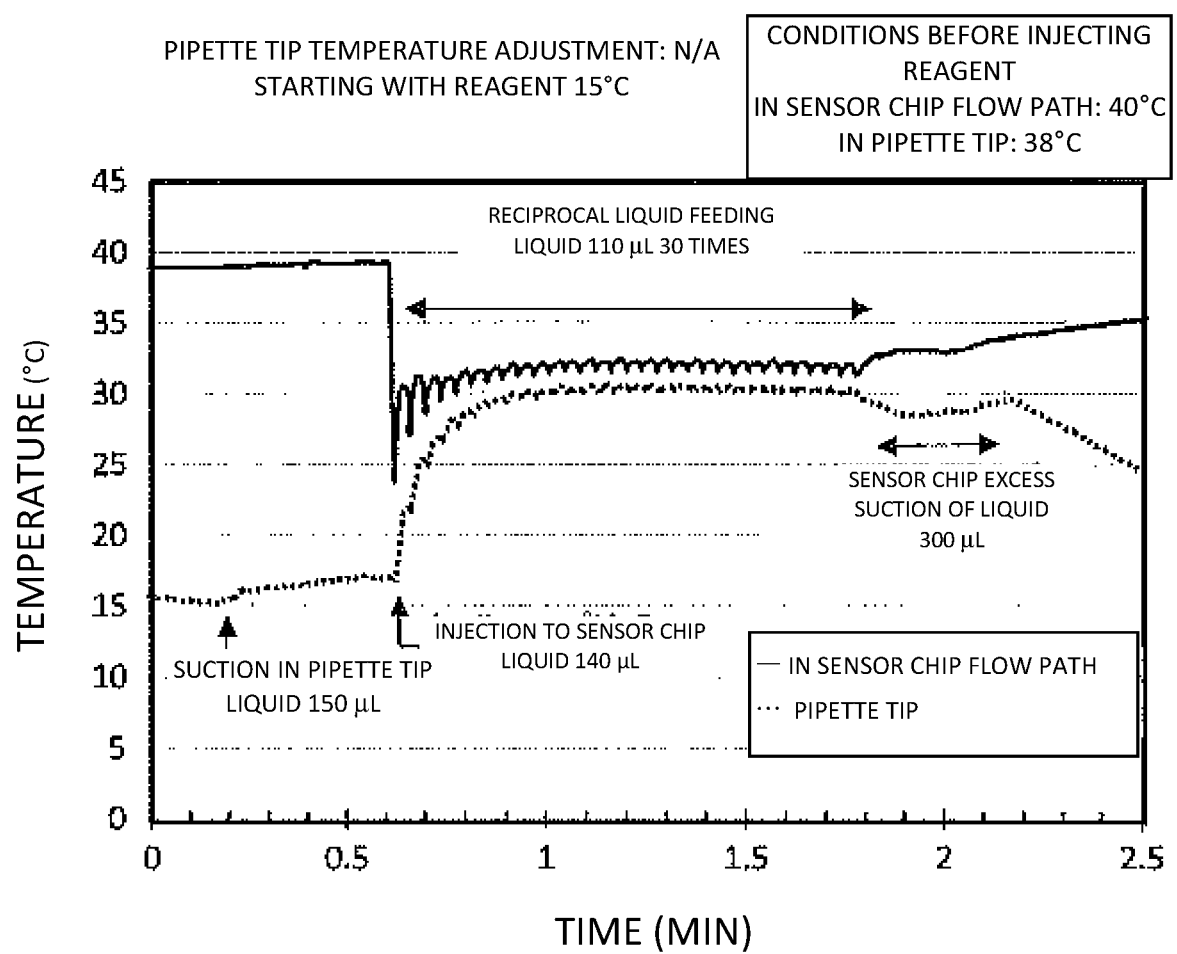
FIG. 8B is a view showing temperature change of a specimen liquid over time at different places in comparative Example 2.

In Comparative Example 1, the steps were performed in the same way as Comparative Example 1 except that the temperature of the specimen liquid for feeding was set to 15° C. It should be noted that the temperature inside the sensor chip was 39° C., which is generally the same temperature as in Examples 1 to 4 and is within a detection error. The resultant chart is shown in FIG. 8B.

Comparative Example 3

Figure 8C:
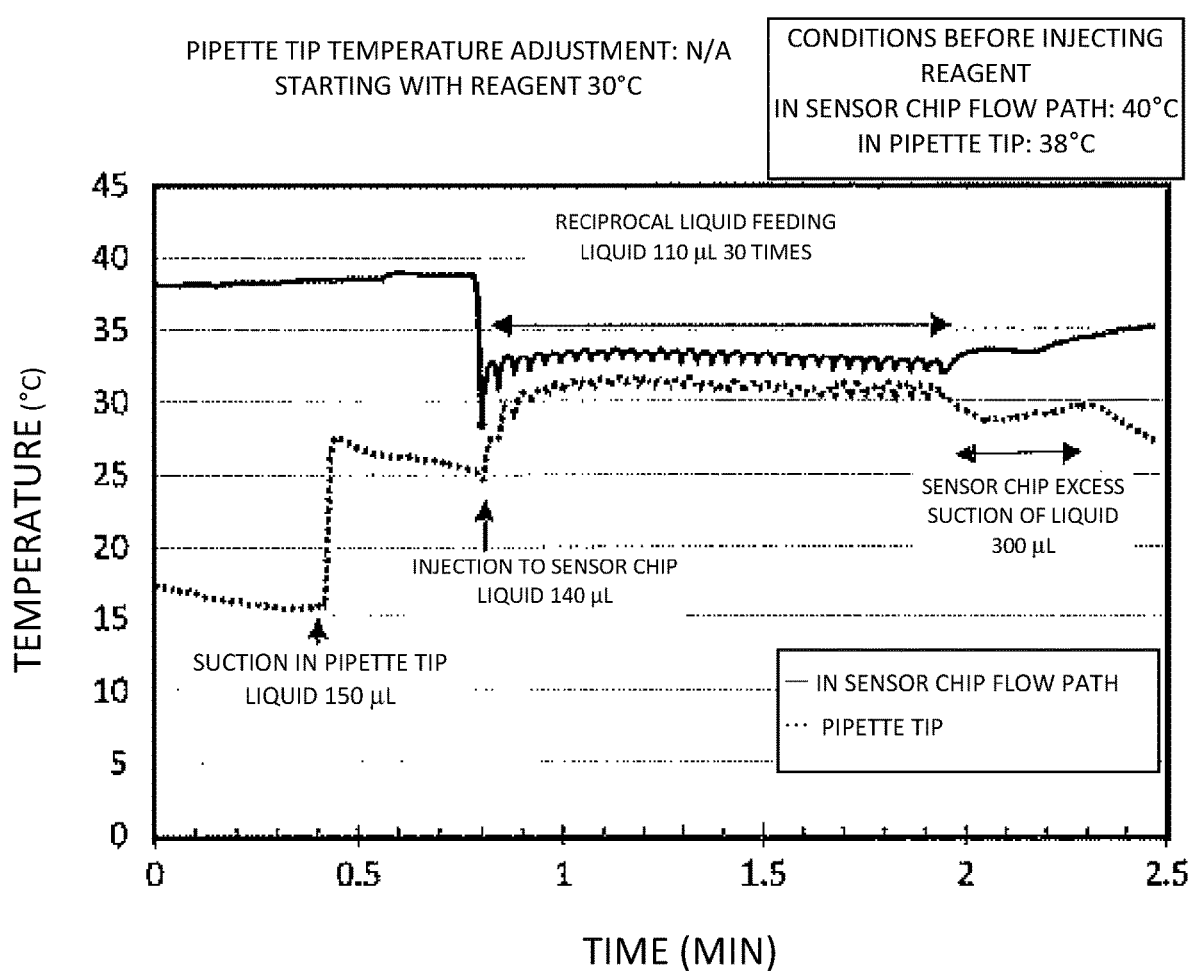
FIG. 8C is a view showing temperature change of a specimen liquid over time at different places in Comparative Example 3.

In Comparative Example 1, the steps were performed in the same way as Comparative Example 1 except that the temperature of the specimen liquid for feeding was set to 30° C. The resultant chart is shown in FIG. 8C.

Comparative Example 4

Figure 8D:
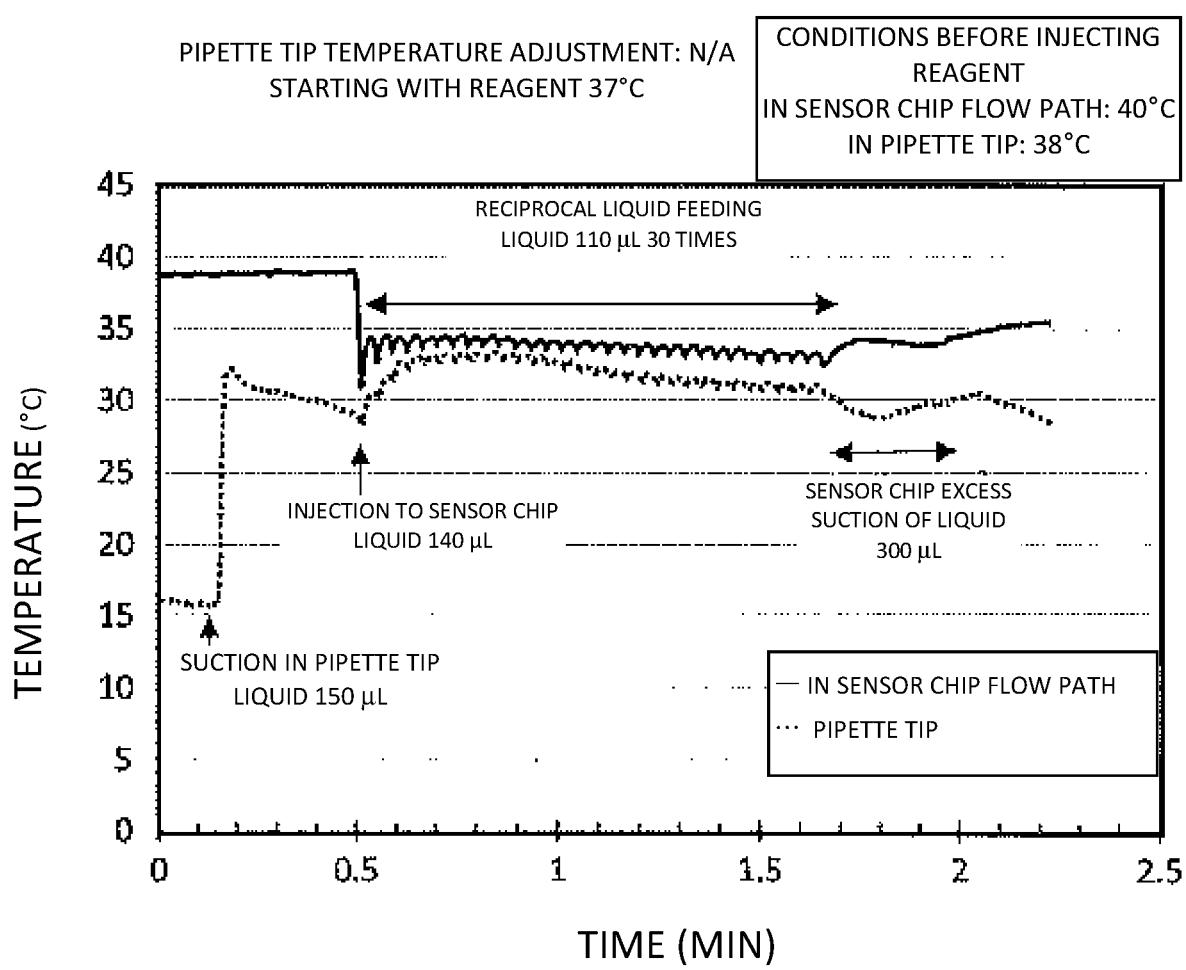
FIG. 8D is a view showing temperature change of a specimen liquid over time at different places in Comparative Example 4.

In Comparative Example 1, the steps were performed in the same way as Comparative Example 1 except that the temperature of the specimen liquid for feeding was set to 37° C. The resultant chart is shown in FIG. 8D.

<Results and Remarks>

When the second temperature adjustment is performed (as in the Examples), even if some of the specimen liquid in the flow path 2 of the sensor chip 1 is transferred inside the pipette tip 10 outside of the flow path 2, the transferred specimen liquid is subjected to the second temperature adjustment in the pipette tip 10, thus, the specimen liquid is not easily affected by the temperature inside the SPFS device 4 (15° C.). Even if a specimen liquid of 5 to 15° C. is used, the temperature of the specimen liquid can be raised to a temperature suitable for a biological reaction (approximately 35 to 37° C.) (Examples 1 to 3). Further, even if a specimen liquid that was pre-adjusted to 37° C. is used, the specimen liquid is not overly heated, maintaining the temperature at 37° C. (Example 4).

Whereas, when the second temperature adjustment is not performed (as in the Comparative Examples), if a specimen liquid of 5 to 15° C. is used, the temperature of the specimen liquid rises up to only approximately 30 to 34° C., which cannot be raised to a temperature suitable for a biological reaction (Comparative Examples 1 to 3). Further, if a specimen liquid that was pre-adjusted to 37° C. is used, the specimen liquid is affected by the temperature in the SPFS device, deviating from the a temperature suitable for a biological reaction (Comparative Example 4). Similar results were obtained from the second reciprocal liquid feeding step.

Therefore, the inspection system according to the present invention allows to obtain a sufficient biological reaction under temperature conditions suitable for the target biological reaction, as well as, to obtain a biological reaction in a temperature suitable for the biological reaction even with a specimen liquid of a varying temperature (e.g., low temperature such as 5 to 15° C.) (i.e., robust for specimen liquids of varying initial temperatures).

INDUSTRIAL APPLICABILITY

The above has described the inspection system of the first to third embodiments of the present invention and examples thereof. The invention is, however, not limited to the above-described inspection system of the first to third embodiments, rather can be applied to any inspection system that includes an inspection device and a sensor chip and performs reciprocal liquid feeding, where at least some of a reaction liquid in a flow path of the sensor chip is caused to flow out of the sensor chip and to flow in again, and may embody the problems addressed by the present invention. In such a case, the inspection system may include, for example, an SPR device or an Attenuated Total Reflection (ATR) device, as a detection system.

REFERENCE SIGNS LIST

1 Sensor chip
2 Flow path
3 Reaction site
4 SPFS device
5 Dielectric member
6 Metallic thin film
7 Minute-flow-path constituting member
8 Liquid discharger/suction unit
9 Liquid mixture
10 Pipette tip
11 Liquid feeder
12 Pump
13 Liquid reservoir
14 Case (liquid feed reaction chamber)
15 Pipette tip conveyance mechanism
16 Light-emitting optical system
17 Light-receiving optical system
18 Case (optical measurement chamber)
19 Partition
20 Opening
21 First heat block
22 Second heat block
22Aa Cutout (opening)
23 Third heat block
24A Controller
24B Memory
25 Light source
26 Angle scanning mechanism
27 Optical control mechanism
28 Group of optical lenses
29 Light detector
30 Sensor control mechanism

The invention claimed is:

1. An inspection system at least comprising:
a sensor chip equipped with a flow path having a reaction site for a biological reaction in at least part of the flow path;
a liquid feeder configured to pump a reaction-liquid used for the biological reaction to flow in and flow out of the flow path of the sensor chip;
a first temperature adjuster configured to adjust a temperature of the reaction liquid in the flow path;
a surface plasmon resonance device configured to receive and inspect the sensor chip after the biological reaction; and
a controller configured to control the operation of the inspection system,
wherein the liquid feeder is also configured to pump, at least some of the reaction liquid that has flowed in the flow path to flow out of the flow path and to flow in again, thereby moving the liquid reciprocally to cause reciprocal liquid feeding of the at least some of the reaction liquid into and out of the flow path of the sensor chip,
the inspection system further comprising: a second temperature adjuster configured to adjust, during the reciprocal liquid feeding, a temperature of the reaction liquid in a liquid holding section of the liquid feeder,
wherein the controller is further configured to monitor and adjust the temperature provided by the first temperature adjuster to maintain a predetermined temperature facilitating the biological reaction on the flow path,
wherein the controller is further configured to monitor and adjust the temperature provided by the second temperature adjuster to maintain the same predetermined temperature facilitating the biological reaction on the flow path, and
wherein a portion of the liquid holding section of the liquid feeder is covered with the second temperature adjuster, and the second temperature adjuster has an opening in a longitudinal wall to receive the portion of the liquid holding section of the liquid feeder.

2. The inspection system according to claim 1, wherein the liquid feeder comprises:
a pump for feeding or sucking the reaction liquid to and from the flow path of the sensor chip; and
a pipette tip as the liquid holding section attached to the pump,
wherein the portion of the longitudinal periphery of the pipette tip to be covered is covered with a heat block serving as the second temperature adjuster.

3. The inspection system according to claim 2, wherein the heat block has the opening in a longitudinal wall to receive the portion of the pipette tip to be covered.

4. The inspection system according to claim 2, wherein the sensor chip has a liquid discharger/suction unit that is provided with a space that communicates with the flow path and houses the tip end of the pipette tip upon insertion into the space of the liquid discharger/suction unit, and
only the portion of the longitudinal periphery of the pipette tip is covered with the heat block so that at least the tip end of the pipette tip, which is inserted in the space of the liquid discharger/suction unit, is exposed.

5. The inspection system according to claim 1, further comprising:
a liquid reservoir that reserves the reaction liquid; and
a third temperature adjuster configured to adjust a temperature of the reaction liquid that is reserved in the liquid reservoir before liquid feeding,
wherein the third temperature adjuster, monitored and adjusted by the controller, adjusts the temperature provided by the third temperature adjuster to the same predetermined temperature as adjusted by the first temperature adjuster.

6. The inspection system according to claim 1, further comprising:
a liquid feed reaction chamber in which the liquid feeder, sensor chip, and the first and second temperature adjusters are arranged inside for performing the biological reaction and temperature adjustments by the first and second temperature adjusters,
an optical measurement chamber in which the surface plasmon resonance device configured to receive the sensor chip after the biological reaction is arranged, the surface plasmon resonance device including (i) a light-emitting unit configured to irradiate the reaction site of the sensor chip with excitement light, and (ii) a light-receiving unit configured to detect light emitted from the irradiated sensor chip arranged inside the optical measurement chamber, the light-receiving unit being further configured to perform optical measurement based on the detected light, and
a partition positioned intermediate the liquid feed reaction chamber and the optical measurement chamber, the partition being configured to open and close an opening that makes the liquid feed reaction chamber and the optical measurement chamber to communicate with each other allowing the transfer of the sensor chip,
wherein the partition closes the opening during the temperature adjustment or the optical measurement.

7. The inspection system according to claim 6, wherein the controller adjusts a temperature of a space inside the optical measurement chamber to be set lower than a temperature of a space inside the liquid feed reaction chamber during the biological reaction.

8. The inspection system according to claim 2, further comprising:
a liquid reservoir that reserves the reaction liquid; and
a third temperature adjuster configured to adjust a temperature of the reaction liquid that is reserved in the liquid reservoir before liquid feeding,
wherein the third temperature adjuster, monitored and adjusted by the controller, adjusts the temperature provided by the third temperature adjuster to the same predetermined temperature as adjusted by the first temperature adjuster.

9. The inspection system according to claim 3, further comprising:
a liquid reservoir that reserves the reaction liquid; and
a third temperature adjuster configured to adjust a temperature of the reaction liquid that is reserved in the liquid reservoir before liquid feeding,
wherein the third temperature adjuster, monitored and adjusted by the controller, adjusts the temperature provided by the third temperature adjuster to the same predetermined temperature as adjusted by the first temperature adjuster.

10. The inspection system according to claim 4, further comprising:
a liquid reservoir that reserves the reaction liquid; and
a third temperature adjuster configured to adjust a temperature of the reaction liquid that is reserved in the liquid reservoir before liquid feeding, wherein the third temperature adjuster, monitored and adjusted by the controller, adjusts the temperature provided by the third temperature adjuster to the same predetermined temperature as adjusted by the first temperature adjuster.

11. The inspection system according to claim 2, further comprising:
a liquid feed reaction chamber in which the liquid feeder, sensor chip, and the first and second temperature adjusters are arranged inside for performing the biological reaction and temperature adjustments by the first and second temperature adjusters,
an optical measurement chamber in which the surface plasmon resonance device configured to receive the sensor chip after the biological reaction is arranged, the surface plasmon resonance device including (i) a light-emitting unit the reaction site of the sensor chip with excitement light, and (ii) a light-receiving unit configured to detect light emitted from the irradiated sensor chip arranged inside the optical measurement chamber, the light-receiving unit being further configured to perform optical measurement based on the detected light, and
a partition positioned intermediate the liquid feed reaction chamber and the optical measurement chamber, the partition being configured to open and close an opening that makes the liquid feed reaction chamber and the optical measurement chamber to communicate with each other allowing the transfer of the sensor chip,
wherein the partition closes the opening during the temperature adjustment or the optical measurement.

12. The inspection system according to claim 3, further comprising:
a liquid feed reaction chamber in which the liquid feeder, sensor chip, and the first and second temperature adjusters are arranged inside for performing the biological reaction and temperature adjustments by the first and second temperature adjusters,
an optical measurement chamber in which the surface plasmon resonance device configured to receive the sensor chip after the biological reaction is arranged, the surface plasmon resonance device including (i) a light-emitting unit configured to irradiate the reaction site of the sensor chip with excitement light, and (ii) a light-receiving unit configured to detect light emitted from the irradiated sensor chip arranged inside the optical measurement chamber, the light-receiving unit being further configured to perform optical measurement based on the detected light, and
a partition positioned intermediate the liquid feed reaction chamber and the optical measurement chamber, the partition being configured to open and close an opening that makes the liquid feed reaction chamber and the optical measurement chamber to communicate with each other allowing the transfer of the sensor chip,
wherein the partition closes the opening during the temperature adjustment or the optical measurement.

13. The inspection system according to claim 4, further comprising:
a liquid feed reaction chamber in which the liquid feeder, the sensor chip, and the first and second temperature adjusters are arranged inside for performing the biological reaction and temperature adjustments by the first and second temperature adjusters,
an optical measurement chamber in which the surface plasmon resonance device configured to receive the sensor chip after the biological reaction is arranged, the surface plasmon resonance device including (i) a light-emitting unit configured to irradiate the reaction site of the sensor chip with excitement light, and (ii) a light-receiving unit configured to detect light emitted from the irradiated sensor chip arranged inside the optical measurement chamber, the light-receiving unit being further configured to perform optical measurement based on the detected light, and
a partition positioned intermediate the liquid feed reaction chamber and the optical measurement chamber, the partition being configured to open and close an opening that makes the liquid feed reaction chamber and the optical measurement chamber to communicate with each other allowing the transfer of the sensor chip,
wherein the partition closes the opening during the temperature adjustment or the optical measurement.

14. The inspection system according to claim 5, further comprising:
a liquid feed reaction chamber in which the liquid feeder, the sensor chip, and the first and second temperature adjusters are arranged inside for performing the biological reaction and temperature adjustments by the first and second temperature adjusters,
an optical measurement chamber in which the surface plasmon resonance device configured to receive the sensor chip after the biological reaction is arranged, the surface plasmon resonance device including (i) a light-emitting unit configured to irradiate the reaction site of the sensor chip with excitement light, and (ii) a light-receiving unit configured to detect light emitted from the irradiated sensor chip arranged inside the optical measurement chamber, the light-receiving unit being further configured to perform optical measurement based on the detected light, and
a partition positioned intermediate the liquid feed reaction chamber and the optical measurement chamber, the partition being configured to open and close an opening that makes the liquid feed reaction chamber and the optical measurement chamber to communicate with each other allowing the transfer of the sensor chip,
wherein the partition closes the opening during the temperature adjustment or the optical measurement.

\* \* \* \* \*